US010640757B2

(12) United States Patent
Jorgensen et al.

(10) Patent No.: US 10,640,757 B2
(45) Date of Patent: May 5, 2020

(54) STABLY MAINTAINED MULTIPLE COPIES OF AT LEAST TWO ORF IN THE SAME ORIENTATION

(71) Applicant: Novozymes A/S, Bagsvaerd (DK)

(72) Inventors: Steen Troels Jorgensen, Allerod (DK); Poul Erik Pedersen, Soborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/034,124

(22) Filed: Sep. 23, 2013

(65) Prior Publication Data

US 2014/0106457 A1 Apr. 17, 2014

Related U.S. Application Data

(63) Continuation of application No. 11/571,091, filed as application No. PCT/DK2005/000409 on Jun. 20, 2005, now abandoned.

(60) Provisional application No. 60/618,487, filed on Oct. 13, 2004, provisional application No. 60/581,834, filed on Jun. 21, 2004.

(30) Foreign Application Priority Data

Jun. 21, 2004 (DK) .............................. 2004 00968
Oct. 13, 2004 (DK) .............................. 2004 01569

(51) Int. Cl.
| | |
|---|---|
| C12N 9/54 | (2006.01) |
| C12N 9/50 | (2006.01) |
| C12N 9/52 | (2006.01) |
| C12N 15/67 | (2006.01) |
| C12N 15/90 | (2006.01) |
| A61K 38/00 | (2006.01) |

(52) U.S. Cl.
CPC .............. *C12N 9/52* (2013.01); *C12N 15/67* (2013.01); *C12N 15/902* (2013.01); *C12N 2800/40* (2013.01); *C12N 2830/20* (2013.01)

(58) Field of Classification Search
None
See application file for complete search history.

(56) References Cited

U.S. PATENT DOCUMENTS

| | | | |
|---|---|---|---|
| 5,324,660 A | 6/1994 | Gleeson et al. | |
| 5,439,810 A | 8/1995 | Loosmore et al. | |
| 5,766,912 A | 6/1998 | Boel et al. | |
| 5,786,464 A | 7/1998 | Seed | |
| 6,114,148 A | 9/2000 | Seed et al. | |
| 6,124,097 A * | 9/2000 | van Eekelen | C12N 9/2417 435/212 |
| 6,534,315 B1 | 3/2003 | Bauer et al. | |
| 6,762,040 B2 | 7/2004 | Rasmussen | |
| 6,808,896 B2 | 10/2004 | Jorgensen et al. | |
| 6,916,917 B1 | 7/2005 | Baltimore et al. | |
| 7,485,447 B2 | 2/2009 | Lassen | |
| 7,521,204 B2 | 4/2009 | Andersen et al. | |
| 2003/0032186 A1* | 2/2003 | Jorgensen | C12N 15/75 435/455 |
| 2003/0032189 A1 | 2/2003 | Jorgensen et al. | |
| 2003/0157641 A1 | 8/2003 | Reff et al. | |
| 2004/0029129 A1* | 2/2004 | Wang | C07K 14/195 435/6.18 |
| 2004/0043458 A1 | 3/2004 | Bathe et al. | |
| 2004/0063186 A1 | 4/2004 | McGrew | |
| 2004/0078837 A1* | 4/2004 | Shannon | C07K 14/4702 800/18 |
| 2004/0091958 A1 | 5/2004 | Van Ooijen et al. | |
| 2004/0214787 A1 | 10/2004 | Chauvaux et al. | |
| 2006/0040346 A1 | 2/2006 | Andersen et al. | |
| 2006/0143738 A1 | 6/2006 | Lassen | |
| 2006/0292566 A1* | 12/2006 | Frazer | C12N 15/67 435/6.11 |
| 2007/0130630 A1 | 6/2007 | Nielsen et al. | |
| 2007/0134760 A1 | 6/2007 | Olsen et al. | |
| 2007/0259404 A1* | 11/2007 | Jorgensen | C12P 21/00 435/71.1 |
| 2008/0085535 A1 | 4/2008 | Breuner et al. | |
| 2008/0193977 A1* | 8/2008 | Finnis | C07K 14/395 435/69.4 |
| 2008/0261861 A1* | 10/2008 | Sleep | C12N 15/81 514/1.1 |

FOREIGN PATENT DOCUMENTS

| | | |
|---|---|---|
| EP | 0 305 216 A1 | 1/1989 |
| EP | 0 523 976 B1 | 1/1993 |
| WO | 91/009129 A1 | 6/1991 |

(Continued)

OTHER PUBLICATIONS

Rey et al. (2004) Maturation of Fibrinolytic Bacillopeptidase F Involves both Heteroand Autocatalytic Processes, Genome Biol., 5:R77, pp. 1-12.*
Meng et al. (2016) Maturation of Fibrinolytic Bacillopeptidase F Involves both Heteroand Autocatalytic Processes, Appl. Environ. Microb.,vol. 82, pp. 318-327.*
Mironczuk et al. (2008) Induction of natural competence in Bacillus cereus ATCC14579, Microbiol. Biotechnol., vol. 1, pp. 226-235.*
Schmid et al. (1995) Alkalophilic *bacillus* sp. Strain LG12 Has a Series of Serine Protease Genes, Appl. Environ. Microb. (1995) vol. 61, pp. 4490-4493.*

(Continued)

*Primary Examiner* — Manjunath N Rao
*Assistant Examiner* — Samuel W Liu
(74) *Attorney, Agent, or Firm* — Eric Fechter

(57) ABSTRACT

The present invention relates to a method for constructing a host cell expressing a polypeptide of interest from at least two ORF's stably integrated onto the chromosome of the host cell comprising the steps of:
  a) providing the at least two ORF's encoding the same polypeptide, wherein the at least two DNA sequences of the ORF's differ in at least one position;
  b) integrating the at least two ORF's in the same orientation on the host cell chromosome.

19 Claims, 1 Drawing Sheet

Specification includes a Sequence Listing.

(56) References Cited

FOREIGN PATENT DOCUMENTS

| WO | 94/014968 A1 | 7/1994 | | |
|---|---|---|---|---|
| WO | 199901562 | 1/1999 | | |
| WO | 199941358 | 8/1999 | | |
| WO | 200078985 | 12/2000 | | |
| WO | 2001011063 A2 | 2/2001 | | |
| WO | 200200907 | 1/2002 | | |
| WO | WO-0200907 A1 * | 1/2002 | ............ | C12N 15/75 |
| WO | 2004111219 A1 | 12/2004 | | |

OTHER PUBLICATIONS

Jung, et al, General and app Microbiology, 44, 107-111 (1998).
Lann, et al, App and Envi Microbiology, 57, 901-90 (1991).
Hone et al., Microbial Pathogenesis, 1988, 5: 407-418.
Ayares et al, 1986, Proc Natl Acad Sci 83, 5199-5203.
Chedin et al, 1994, Molecular Microbiology 12(4), 561-56.
Chen et al, 1994, J America Chem Soc 116, 8799-8880.
Khasanov et al, 1992, Mol Gen Genet 234, 494-497.
Puchta et al, 1991, Nucl Acids Res 19(10), 2693-2700.
Stemmer et al. 1995, Gene 165, 49-53.
Watt et al, 1985, Proc Acad Natl Sci 82, 4768-4772.
Zhang et al, 2005, Progress Nat Sci 15(9), 798-803.

* cited by examiner

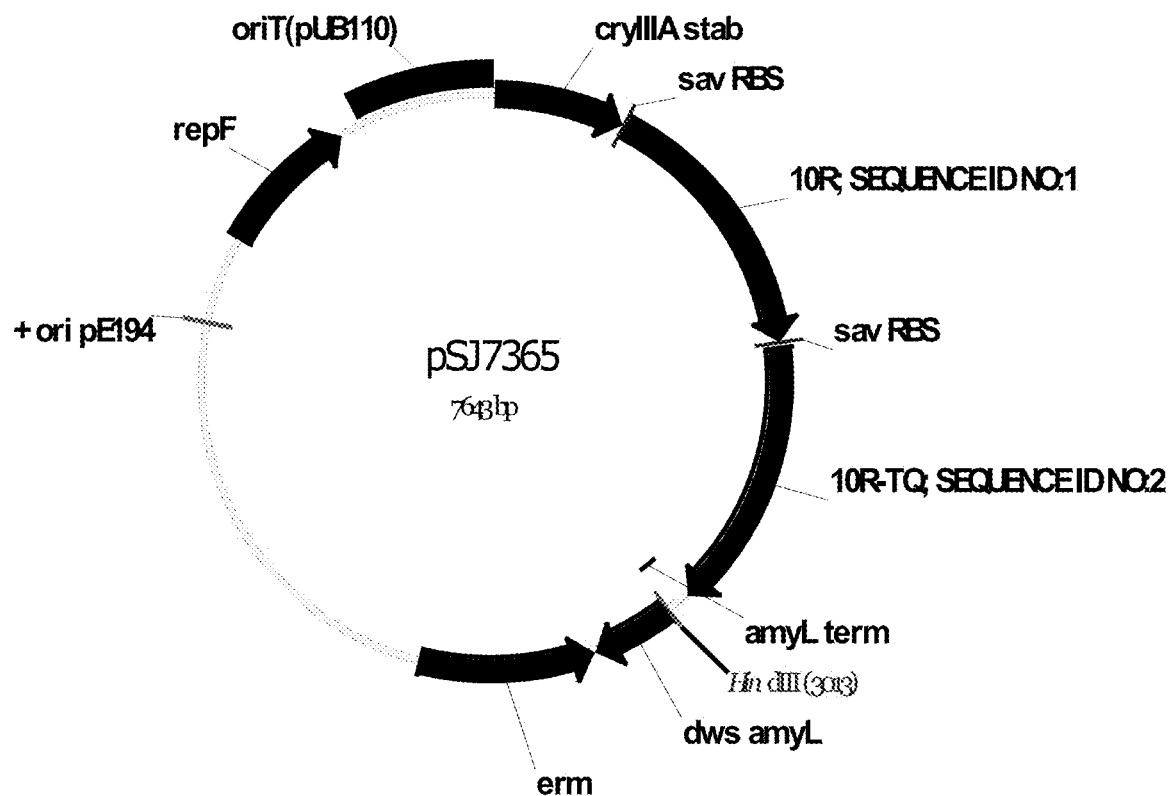

SEQUENCE LISTING

```
<160> NUMBER OF SEQ ID NOS: 55

<210> SEQ ID NO 1
<211> LENGTH: 1140
<212> TYPE: DNA
<213> ORGANISM: Artificial Sequence
<220> FEATURE:
<223> OTHER INFORMATION: Protease 10R encoding sequence

<400> SEQUENCE: 1
atgaaaaaac cgctgggaaa aattgtcgca agcacagcac ttcttatttc agtggcattt      60
agctcatcta ttgcatcagc agctacagga gcattaccgc agtctccgac accggaagca     120
gatgcagtct caatgcaaga agcactgcaa agagatcttg atcttacatc agcagaagca     180
gaagaacttc ttgctgcaca agatacagca tttgaagtgg atgaagcagc ggcagaagca     240
gcaggagatg catatggcgg ctcagttttt gatacagaat cacttgaact tacggttctt     300
gttacagatg cagcagcagt tgaagcagtt gaagcaacag gagcaggaac agaacttgtt     360
tcatatggaa ttgatggcct tgatgaaatt gttcaagaac tgaatgcagc tgatgctgtt     420
ccgggcgttg ttggctggta tccggatgtt gctggagata cagttgtcct tgaagttctt     480
gaaggatcag gcgcagatgt ttcaggcctg ctggcagatg caggagtcga tgcatcagca     540
gttgaagtta caacatcaga tcaaccggaa ctttatgcag atattattgg cggcctggca     600
tatacaatgg gcggcagatg cagcgttggc tttgcagcaa caaatgcagc aggccaaccg     660
ggctttgtta cagcaggcca ttgcggcaga gttggcacac aggttacaat tggcaatggc     720
agaggcgttt ttgaacaaag cgtttttccg ggcaatgatg cagcatttgt tagaggcaca     780
tcaaatttta cacttacaaa tctggtttca agatataata caggcggcta tgcaacagtt     840
gcaggccata atcaagcacc gattggctca tcagtttgca gatcaggctc aacaacaggc     900
tggcattgcg gcacaattca agcaagaggc aaagcgttta gctatccgga aggcacagtt     960
acaaatatga caagaacaac agtttgtgca gaaccgggcg attcaggcgg ctcatatatt    1020
agcggcacac aagcacaagg cgttacatca ggcggctcag gcaattgcag aacaggcggc    1080
acaacatttt accaagaagt tacaccgatg gttaattcat ggggcgttag acttagaaca    1140
```

```
<210> SEQ ID NO 2
<211> LENGTH: 1146
<212> TYPE: DNA
<213> ORGANISM: Artificial Sequence
<220> FEATURE:
<223> OTHER INFORMATION: Protease 10R with 2 as C-terminal extension

<400> SEQUENCE: 2
atgaagaaac cgttggggaa aattgtcgca agcaccgcac tactcatttc tgttgctttt       60
agttcatcga tcgcatcggc tgctactgga gcattacctc agtctcctac acctgaagca      120
gatgcagtat cgatgcaaga agcattacaa cgtgatcttg atcttacatc agctgaagct      180
gaggaattac ttgctgcaca agatacagcc tttgaagttg atgaagctgc cgctgaagca      240
gctggtgatg catatggtgg ttcagtattc gatactgaat cactcgaact tactgtacta      300
gtgaccgatg cagcagctgt tgaagctgtt gaagccacag gtgcaggtac agagctcgta      360
tcttatggta ttgatggatt agatgagatc gtacaagagc ttaatgcagc tgatgccgtt      420
ccaggtgtag ttggatggta tcctgatgta gcaggtgata ctgttgtctt agaagttctt      480
gaaggctctg gagctgatgt ttctggactt ttagcagacg caggagtcga tgcatccgcg      540
gttgaagtga ccacgtcaga tcagcctgaa ctctatgccg atatcattgg aggcctagcg      600
tacacaatgg gtggtcgctg cagcgtagga tttgcagcca caaatgcagc tggacaacct      660
ggcttcgtga cagctggaca ttgcggccgc gtcggtacac aggttactat cggcaatgga      720
agaggtgtct ttgagcaaag cgtatttccc gggaatgatg ctgccttcgt tagaggtacg      780
tccaacttta cgcttactaa cttagtatct agatacaaca ctggcggata tgcaactgta      840
gcaggtcaca atcaagcacc tattggctct agcgtctgcc gctcagggtc gactacagga      900
tggcattgtg aaccattca gctagaggt cagagcgtga gctatcctga aggtaccgta      960
acgaacatga ctcgtacgac tgtatgtgca gaaccaggtg actctggagg ttcatatatc     1020
agcggtacgc aagcgcaagg cgttacctca ggtggatccg gtaactgtag gacaggtggc     1080
acaacgttct accaggaagt gacaccgatg gtgaactctt ggggagttag actccgtaca     1140
acacaa                                                                 1146

<210> SEQ ID NO 3
<211> LENGTH: 1143
<212> TYPE: DNA
<213> ORGANISM: Artificial Sequence
<220> FEATURE:
<223> OTHER INFORMATION: Protease 10R encoding sequence

<400> SEQUENCE: 3
atgaaaaaac cgctgggaaa aattgtcgca agcacagcac ttcttatttc agtggcattt       60
agctcatcta ttgcatcagc tgctacggga gctttaccgc agtctccgac accggaagca      120
gatgcagtgt caatgcaaga agcactgcaa agagatcttg atcttacatc agcagaagca      180
gaagaacttc ttgctgcaca agatacagca tttgaagtgg atgaagcagc ggcagaagca      240
gcaggagatg catatggcgg ctcagttttt gatacagaat cacttgaact tacggttctt      300
gttacagatg cagcagcagt tgaagcagtt gaagcaacag gtgcaggaac agaacttgtt      360
tcatatggaa ttgatggcct tgatgaaatt gttcaagaac tgaatgcagc tgatgctgtt      420
ccgggcgttg tcggctggta tccggatgtt gctggagata cagttgtcct tgaagttctt      480
gaaggatcag gcgcagatgt ttcaggcctg ctgcagatg caggagtcga tgcatcagca      540
gttgaagtta caacatcaga tcaaccggaa ctttatgcag atattattgg cggcctggca      600
```

| | |
|---|---|
| tatacaatgg gcggcagatg cagcgttggc tttgcagcaa caaatgcagc aggccaaccg | 660 |
| ggctttgtta cagcaggcca ttgcggcaga gttggcacac aggttacaat tggcaatggc | 720 |
| agaggcgttt ttgaacaaag cgttttccg gcaatgatg cagcatttgt tagaggcaca | 780 |
| tcaaatttta cacttacaaa tctggtttca agatataata caggcggcta tgcaacagtt | 840 |
| gcaggccata atcaagcacc gattggctca tcagtttgca gatcaggctc aacaacaggc | 900 |
| tggcattgcg gcacaattca agcaagaggc caaagcgtta gctatccgga aggcacagtt | 960 |
| acaaatatga caagaacaac agtttgtgca gaaccgggcg attcaggcgg ctcatatatt | 1020 |
| agcggcacac aagcacaagg cgttacatca ggcggctcag gcaattgcag aacaggcggc | 1080 |
| acaacatttt accaagaagt tacaccgatg gttaattcat ggggcgttag acttagaaca | 1140 |
| taa | 1143 |

<210> SEQ ID NO 4
<211> LENGTH: 1143
<212> TYPE: DNA
<213> ORGANISM: Artificial Sequence
<220> FEATURE:
<223> OTHER INFORMATION: Protease 10R encoding sequence

<400> SEQUENCE: 4

| | |
|---|---|
| atgaaaaaac cgctgggaaa aattgtcgca agcacagcac ttcttatttc agtggcattt | 60 |
| agctccagca ttgcatcagc tgctacggga gctttaccgc agtctccgac accggaagca | 120 |
| gatgcagtgt caatgcaaga agcactgcaa agagatcttg atcttacatc agcagaagca | 180 |
| gaagaacttc ttgctgcaca agatacagca tttgaagtgg atgaagcagc ggcagaagca | 240 |
| gcaggagatg catatggcgg ctcagttttt gatacagaat cacttgaact tacggttctt | 300 |
| gttacagatg cagcagcagt tgaagcagtt gaagcaacag gtgcaggaac agaacttgtt | 360 |
| tcatatggaa ttgatggcct tgatgaaatt gttcaagaac tgaatgcagc tgatgctgtt | 420 |
| ccgggcgttg tcggctggta tccggatgtt gctggagata cagttgtcct tgaagttctt | 480 |
| gaaggatcag gcgcagatgt ttcaggcctg ctggcagatg caggagtcga tgcatcagca | 540 |
| gttgaagtta caacatcaga tcaaccggaa ctttatgcag atattattgg cggcctggca | 600 |
| tatacaatgg gcggcagatg cagcgttggc tttgcagcaa caaatgcagc aggccaaccg | 660 |
| ggctttgtta cagcaggcca ttgcggcaga gttggcacac aggttacaat tggcaatggc | 720 |
| agaggcgttt ttgaacaaag cgttttccg gcaatgatg cagcatttgt tagaggcaca | 780 |
| tcaaatttta cacttacaaa tctggtttca agatataata caggcggcta tgcaacagtt | 840 |
| gcaggccata atcaagcacc gattggctca tcagtttgca gatcaggctc aacaacaggc | 900 |
| tggcattgcg gcacaattca agcaagaggc caaagcgtta gctatccgga aggcacagtt | 960 |
| acaaatatga caagaacaac agtttgtgca gaaccgggcg attcaggcgg ctcatatatt | 1020 |
| agcggcacac aagcacaagg cgttacatca ggcggctcag gcaattgcag aacaggcggc | 1080 |
| acaacatttt accaagaagt tacaccgatg gttaattcat ggggcgtgcg ccttcgcaca | 1140 |
| taa | 1143 |

<210> SEQ ID NO 5
<211> LENGTH: 1143
<212> TYPE: DNA
<213> ORGANISM: Artificial Sequence
<220> FEATURE:
<223> OTHER INFORMATION: Protease 10R encoding sequence

<400> SEQUENCE: 5

```
atgaaaaaac cgctgggaaa aattgtcgca agcacagcac ttcttatttc agtggcattt    60
agctcatcta ttgcatcagc agctacagga gcattaccgc agtctccgac accggaagca   120
gatgcagtct caatgcaaga agcactgcaa agagatcttg atcttacatc agcagaagca   180
gaagaacttc ttgctgcaca agatacagca tttgaagtgg atgaagcagc ggcagaagca   240
gcaggagatg catatggcgg ctcagttttt gatacagaat cacttgaact tacggttctt   300
gttacagatg cagcagcagt tgaagcagtt gaagcaacag gagcaggaac agaacttgtt   360
tcatatggaa ttgatggcct tgatgaaatt gttcaagaac tgaatgcagc tgatgctgtt   420
ccgggcgttg ttggctggta tccggatgtt gctggagata cagttgtcct tgaagttctt   480
gaaggatcag gcgcagatgt ttcaggcctg ctggcagatg caggagtcga tgcatcagca   540
gttgaagtta aacatcaga tcaaccggaa ctttatgcag atattattgg cggcctggca   600
tatacaatgg gcggcagatg cagcgttggc tttgctgcaa caaatgcagc aggccaaccg   660
ggctttgtta cagcaggcca ttgcggcaga gttggcacac aggttacaat ggcaatggc   720
agaggcgttt ttgaacaaag cgttttttccg gcaatgatg cagcatttgt tagaggcaca   780
tcaaatttta cacttacaaa cctggtttca agatataata caggcggcta tgcaacagtt   840
gcaggccata atcaagcacc gattggctca tcagtttgca gatcaggctc aacaacaggc   900
tggcattgcg gcacaattca agcaagaggc caaagcgtta gctatccgga aggcacagtt   960
acaaatatga caagaacaac agtctgtgcc gaaccgggcg attcaggcgg ctcatatatt  1020
agcggcacgc aggcgcaagg cgttacatca ggcggctcag gcaattgcag aacaggcggc  1080
actacatttt accaagaagt tacaccgatg gtaaattcat ggggcgtgcg ccttcgcaca  1140
taa                                                                1143
```

<210> SEQ ID NO 6
<211> LENGTH: 1143
<212> TYPE: DNA
<213> ORGANISM: Artificial Sequence
<220> FEATURE:
<223> OTHER INFORMATION: Protease 10R encoding sequence

<400> SEQUENCE: 6

```
atgaaaaaac cgttgggaaa aattgtggca agcacagcat tgttaattag cgtggcattt    60
agcagcagca ttgcaagcgc agcaacagga gcattgccgc aaagcccgac accggaagca   120
gatgcagtga gcatgcaaga agcattgcaa agagatttgg atttgacaag cgcagaagca   180
gaagaattgt tagcagcaca agatacagca tttgaagtgg atgaagcagc agcagaagca   240
gcaggagatg catatggagg aagcgtgttt gatacagaga gcttggaatt gacagtgtta   300
gtgacagatg cagcagcagt ggaagcagtg gaagcaacag gagcaggaac agaattggtg   360
agctatggaa ttgatggatt agatgaaatt gtgcaagaat tgaatgcagc agatgcagtg   420
ccgggagtgg tgggatggta tccggatgtg gcaggagata cagtggtgtt agaagtgtta   480
gaaggaagcg gagcagatgt gagcggattg ttggcagatg caggagtgga tgcaagcgca   540
gtggaagtga caacaagcga tcaaccggaa ttatatgcag atattattgg aggattagca   600
tatacaatgg gaggaagatg cagcgtggga tttgcagcaa caaatgcagc aggacaaccg   660
ggatttgtga cagcaggaca ttgcggaaga gtgggaacac aagtgacaat ggaaatggga   720
agaggagtgt ttgaacaaag cgtgttttccg ggaaatgatg cagcatttgt gagaggaaca   780
agcaattta cattaacaaa tttggtgagc agatataata caggaggata tgcaacagtg   840
```

```
gcaggacata atcaagcacc gattggaagc agcgtgtgca gaagcggaag cacaacagga    900
tggcattgcg gaacaattca agcaagagga caaagcgtga gctatccgga aggaacagtg    960
acaaatatga caagaacaac agtgtgcgca gaaccgggag atagcggagg aagctatatt   1020
agcggaacac aagcacaagg agtgacaagc ggaggaagcg gaaattgcag aacaggagga   1080
acaacatttt atcaagaagt gacaccgatg gtgaatagct ggggagtgag attgagaaca   1140
taa                                                                 1143

<210> SEQ ID NO 7
<211> LENGTH: 1143
<212> TYPE: DNA
<213> ORGANISM: Artificial Sequence
<220> FEATURE:
<223> OTHER INFORMATION: Protease 10R encoding sequence

<400> SEQUENCE: 7
atgaaaaaac cgttgggaaa aattgtggca agcacagcat tgttaattag cgtggcattt     60
agcagcagca ttgcaagcgc agcaacagga gcattgccgc aaagcccgac accggaagca    120
gatgcagtga gcatgcaaga agcattgcaa agagatttgg atttgacaag cgcagaagca    180
gaagaattgt tagcagcaca agatacagca tttgaagtgg atgaagcagc agcagaagca    240
gcaggagatg catatggagg aagcgtgttt gatacagaga gcttggaatt gacagtgtta    300
gtgacagatg cagcagcagt ggaagcagtg gaagcaacag gagcaggaac agaattggtg    360
agctatggaa ttgatggatt agatgaaatt gtgcaagaat tgaatgcagc agatgcagtg    420
ccgggagtgg tgggatggta tccggatgtg gcaggagata cagtggtgtt agaagtgtta    480
gaaggaagcg gagcagatgt gagcggattg ttggcagatg caggagtgga tgcaagcgca    540
gtggaagtga acaacaagcga tcaaccggaa ttatatgcag atattattgg aggattagca    600
tatacaatgg gaggaagatg cagcgtggga tttgcagcaa caaatgcagc aggacaaccg    660
ggatttgtga cagcaggaca ttgcggaaga gtgggaacac aagtgacaat ggaaatggaa    720
agaggagtgt ttgaacaaag cgtgtttccg ggaaatgatg cagcatttgt gagaggaaca    780 agcaattttta cattaacaaa tttggtgagc agatataata caggaggata tgcaacagtg    840
gcaggacata atcaagcacc gattggaagc agcgtgtgca gaagcggaag cacaacagga    900
tggcattgcg gaacaattca agcaagagga caaagcgtga gctatccgga aggaacagtg    960
acaaatatga caagaacaac agtgtgcgca gaaccgggag atagcggagg aagctatatt   1020
agcggaacac aagcacaagg agtgacaagc ggaggaagcg gaaattgcag aacaggagga   1080
acaacatttt atcaagaagt gacaccgatg gtgaatagct ggggagtgag attgagaaca   1140
taa                                                                 1143

<210> SEQ ID NO 8
<211> LENGTH: 1148
<212> TYPE: DNA
<213> ORGANISM: Artificial Sequence
<220> FEATURE:
<223> OTHER INFORMATION: Protease 10R encoding sequence comprising
      MluI-site

<400> SEQUENCE: 8
atgaagaaac cgttgggggaa aattgtcgca agcaccgcac tactcatttc tgttgctttt     60
agttcatcga tcgcatcggc tgctactgga gcattacctc agtctcctac acctgaagca    120
gatgcagtat cgatgcaaga agcattacaa cgtgatcttg atcttacatc agctgaagct    180
```

```
gaggaattac ttgctgcaca agatacagcc tttgaagttg atgaagctgc cgctgaagca     240
gctggtgatg catatggtgg ttcagtattc gatactgaat cactcgaact tactgtacta     300
gtgaccgatg cagcagctgt tgaagctgtt gaagccacag gtgcaggtac agagctcgta     360
tcttatggta ttgatggatt agatgagatc gtacaagagc ttaatgcagc tgatgccgtt     420
ccaggtgtag ttggatggta tcctgatgta gcaggtgata ctgttgtctt agaagttctt     480
gaaggctctg gagctgatgt ttctggactt ttagcagacg caggagtcga tgcatccgcg     540
gttgaagtga ccacgtcaga tcagcctgaa ctctatgccg atatcattgg aggcctagcg     600
tacacaatgg gtggtcgctg cagcgtagga tttgcagcca caaatgcagc tggacaacct     660
ggcttcgtga cagctggaca ttgcggccgc gtcggtacac aggttactat cggcaatgga     720
agaggtgtct ttgagcaaag cgtatttccc gggaatgatg ctgccttcgt tagaggtacg     780
tccaacttta cgcttactaa cttagtatct agatacaaca ctggcggata tgcaactgta     840
gcaggtcaca atcaagcacc tattggctct agcgtctgcc gctcagggtc gactacagga     900
tggcattgtg gaaccattca agctagaggt cagagcgtga gctatcctga aggtaccgta     960
acgaacatga ctcgtacgac tgtatgtgca gaaccaggtg actctggagg ttcatatatc    1020
agcggtacgc aagcgcaagg cgttacctca ggtggatccg gtaactgtag acaggtggc     1080 acaacgttct accaggaagt gacaccgatg gtgaactctt ggggagttag actccgtaca    1140
taacgcgt                                                             1148

<210> SEQ ID NO 9
<211> LENGTH: 60
<212> TYPE: DNA
<213> ORGANISM: Artificial Sequence
<220> FEATURE:
<223> OTHER INFORMATION: PCR-primer

<400> SEQUENCE: 9
gactctgcag ccgcggacgc gtgctagcgg ccgcgtcgac tagaagagca gagaggacgg     60

<210> SEQ ID NO 10
<211> LENGTH: 49
<212> TYPE: DNA
<213> ORGANISM: Artificial Sequence
<220> FEATURE:
<223> OTHER INFORMATION: PCR-primer

<400> SEQUENCE: 10
gactaagctt atcgatgatc aagatctcaa cgaaatttat aagacgggc                 49

<210> SEQ ID NO 11
<211> LENGTH: 30
<212> TYPE: DNA
<213> ORGANISM: Artificial Sequence
<220> FEATURE:
<223> OTHER INFORMATION: PCR-primer

<400> SEQUENCE: 11
aattggcgcc tgtccagact gtccgctgtg                                      30

<210> SEQ ID NO 12
<211> LENGTH: 36
<212> TYPE: DNA
<213> ORGANISM: Artificial Sequence
<220> FEATURE:
<223> OTHER INFORMATION: PCR-primer

<400> SEQUENCE: 12
```

-continued

```
gattaacgcg ttatgtacgg agtctaactc cccaag                              36
```

<210> SEQ ID NO 13
<211> LENGTH: 42
<212> TYPE: DNA
<213> ORGANISM: Artificial Sequence
<220> FEATURE:
<223> OTHER INFORMATION: PCR-primer

<400> SEQUENCE: 13

```
gactgaattc agatctaaag ataatatctt tgaattgtaa cg                       42
```

<210> SEQ ID NO 14
<211> LENGTH: 33
<212> TYPE: DNA
<213> ORGANISM: Artificial Sequence
<220> FEATURE:
<223> OTHER INFORMATION: PCR-primer

<400> SEQUENCE: 14

```
gactgctagc acgcgttatg tacggagtct aac                                 33
```

<210> SEQ ID NO 15
<211> LENGTH: 64
<212> TYPE: DNA
<213> ORGANISM: Artificial Sequence
<220> FEATURE:
<223> OTHER INFORMATION: PCR-primer

<400> SEQUENCE: 15

```
gactgaattc gagctctata aaatgagga gggaaccgaa tgaaaaaacc gctgggaaaa     60
attg                                                                 64
```

<210> SEQ ID NO 16
<211> LENGTH: 37
<212> TYPE: DNA
<213> ORGANISM: Artificial Sequence
<220> FEATURE:
<223> OTHER INFORMATION: PCR-primer

<400> SEQUENCE: 16

```
gactaagctt acgcgttatg ttctaagtct aacgccc                             37
```

<210> SEQ ID NO 17
<211> LENGTH: 84
<212> TYPE: DNA
<213> ORGANISM: Artificial Sequence
<220> FEATURE:
<223> OTHER INFORMATION: PCR-primer

<400> SEQUENCE: 17

```
gactgaattc agatctacgc gtccatgggc tagcgcggcc gcgtcgacag gcctctttga    60
ttacatttta taattaattt taac                                           84
```

<210> SEQ ID NO 18
<211> LENGTH: 84
<212> TYPE: DNA
<213> ORGANISM: Artificial Sequence
<220> FEATURE:
<223> OTHER INFORMATION: PCR-primer

<400> SEQUENCE: 18

```
gactgaattc atgcataaac tgcatccctt acttgttttt cgtgtgccta tttttgtgaa    60
```
tcgacgtccc gaatacaacg acac                                              84

<210> SEQ ID NO 19
<211> LENGTH: 42
<212> TYPE: DNA
<213> ORGANISM: Artificial Sequence
<220> FEATURE:
<223> OTHER INFORMATION: PCR-primer

<400> SEQUENCE: 19
gactgaattc agatctaaag ataatatctt tgaattgtaa cg                          42

<210> SEQ ID NO 20
<211> LENGTH: 46
<212> TYPE: DNA
<213> ORGANISM: Artificial Sequence
<220> FEATURE:
<223> OTHER INFORMATION: PCR-primer

<400> SEQUENCE: 20
gactaagctt acgcgtctat tgtgttgtac ggagtctaac tcccca                      46

<210> SEQ ID NO 21
<211> LENGTH: 39
<212> TYPE: DNA
<213> ORGANISM: Artificial Sequence
<220> FEATURE:
<223> OTHER INFORMATION: PCR-primer

<400> SEQUENCE: 21
gactgaattc acgcgtgagc tctataaaaa tgaggaggg                              39

<210> SEQ ID NO 22
<211> LENGTH: 36
<212> TYPE: DNA
<213> ORGANISM: Artificial Sequence
<220> FEATURE:
<223> OTHER INFORMATION: PCR-primer

<400> SEQUENCE: 22
gactaagctt gctagcctaa tgtgttgtac ggagtc                                 36

<210> SEQ ID NO 23
<211> LENGTH: 27
<212> TYPE: DNA
<213> ORGANISM: Artificial Sequence
<220> FEATURE:
<223> OTHER INFORMATION: PCR-primer

<400> SEQUENCE: 23
gtccttcttg gtacctggaa gcagagc                                           27

<210> SEQ ID NO 24
<211> LENGTH: 39
<212> TYPE: DNA
<213> ORGANISM: Artificial Sequence
<220> FEATURE:
<223> OTHER INFORMATION: PCR-primer

<400> SEQUENCE: 24
gtataaatat tcggccctta aggccagtac cattttccc                              39

<210> SEQ ID NO 25
<211> LENGTH: 59
<212> TYPE: DNA
<213> ORGANISM: Artificial Sequence

```
<220> FEATURE:
<223> OTHER INFORMATION: PCR-primer

<400> SEQUENCE: 25
tggtactggc cttaagggcc gaatatttat acaatatcat gagctccaca ttgaaaggg      59

<210> SEQ ID NO 26
<211> LENGTH: 34
<212> TYPE: DNA
<213> ORGANISM: Artificial Sequence
<220> FEATURE:
<223> OTHER INFORMATION: PCR-primer

<400> SEQUENCE: 26
ggtgttctct agagcggccg cggttgcggt cagc                                 34

<210> SEQ ID NO 27
<211> LENGTH: 33
<212> TYPE: DNA
<213> ORGANISM: Artificial Sequence
<220> FEATURE:
<223> OTHER INFORMATION: PCR-primer

<400> SEQUENCE: 27
ggccttaagg gcctgctgtc cagactgtcc gct                                  33

<210> SEQ ID NO 28
<211> LENGTH: 18
<212> TYPE: DNA
<213> ORGANISM: Artificial Sequence
<220> FEATURE:
<223> OTHER INFORMATION: PCR-primer

<400> SEQUENCE: 28
ggcgttacaa ttcaaaga                                                   18

<210> SEQ ID NO 29
<211> LENGTH: 37
<212> TYPE: DNA
<213> ORGANISM: Artificial Sequence
<220> FEATURE:
<223> OTHER INFORMATION: PCR-primer

<400> SEQUENCE: 29
ccaggcctta agggccgcat gcgtccttct ttgtgct                              37

<210> SEQ ID NO 30
<211> LENGTH: 27
<212> TYPE: DNA
<213> ORGANISM: Artificial Sequence
<220> FEATURE:
<223> OTHER INFORMATION: PCR-primer

<400> SEQUENCE: 30
gagctccttt caatgtgata catatga                                         27

<210> SEQ ID NO 31
<211> LENGTH: 18
<212> TYPE: DNA
<213> ORGANISM: Artificial Sequence
<220> FEATURE:
<223> OTHER INFORMATION: PCR-primer

<400> SEQUENCE: 31
ggaagtacaa aaataagc                                                   18
```

```
<210> SEQ ID NO 32
<211> LENGTH: 24
<212> TYPE: DNA
<213> ORGANISM: Artificial Sequence
<220> FEATURE:
<223> OTHER INFORMATION: PCR-primer

<400> SEQUENCE: 32
gaattcgacg gcttcccgtg cgcc                                          24

<210> SEQ ID NO 33
<211> LENGTH: 35
<212> TYPE: DNA
<213> ORGANISM: Artificial Sequence
<220> FEATURE:
<223> OTHER INFORMATION: PCR-primer

<400> SEQUENCE: 33
gcaagcgagc acggattgta agtacaagtt agata                              35

<210> SEQ ID NO 34
<211> LENGTH: 35
<212> TYPE: DNA
<213> ORGANISM: Artificial Sequence
<220> FEATURE:
<223> OTHER INFORMATION: PCR-primer

<400> SEQUENCE: 34
aacttgtact tacaatccgt gctcgcttgc cgtac                              35

<210> SEQ ID NO 35
<211> LENGTH: 28
<212> TYPE: DNA
<213> ORGANISM: Artificial Sequence
<220> FEATURE:
<223> OTHER INFORMATION: PCR-primer

<400> SEQUENCE: 35
aagcttccat tcaaacctgg tgaggaag                                      28

<210> SEQ ID NO 36
<211> LENGTH: 34
<212> TYPE: DNA
<213> ORGANISM: Artificial Sequence
<220> FEATURE:
<223> OTHER INFORMATION: PCR-primer

<400> SEQUENCE: 36
catgctgggc ccttaaggcc agtaccattt tccc                               34

<210> SEQ ID NO 37
<211> LENGTH: 69
<212> TYPE: DNA
<213> ORGANISM: Artificial Sequence
<220> FEATURE:
<223> OTHER INFORMATION: PCR-primer

<400> SEQUENCE: 37
cagtaggcct taagggccca gcatgattga gctcaccacc atgggatccg cggccgcaca   60
agggaaggc                                                           69

<210> SEQ ID NO 38
<211> LENGTH: 24
<212> TYPE: DNA
<213> ORGANISM: Artificial Sequence
```

```
<220> FEATURE:
<223> OTHER INFORMATION: PCR-primer

<400> SEQUENCE: 38
caattcatcc tctagagtct cagg                                              24

<210> SEQ ID NO 39
<211> LENGTH: 30
<212> TYPE: DNA
<213> ORGANISM: Artificial Sequence
<220> FEATURE:
<223> OTHER INFORMATION: PCR-primer

<400> SEQUENCE: 39
cgagctcgat gtgttataaa ttgagaggag                                        30

<210> SEQ ID NO 40
<211> LENGTH: 32
<212> TYPE: DNA
<213> ORGANISM: Artificial Sequence
<220> FEATURE:
<223> OTHER INFORMATION: PCR-primer

<400> SEQUENCE: 40
gcggccgcgt cataaacgtt gcaatcgtgc tc                                     32

<210> SEQ ID NO 41
<211> LENGTH: 19
<212> TYPE: DNA
<213> ORGANISM: Artificial Sequence
<220> FEATURE:
<223> OTHER INFORMATION: PCR-primer

<400> SEQUENCE: 41
gtcgaatatg atggggatg                                                    19

<210> SEQ ID NO 42
<211> LENGTH: 35
<212> TYPE: DNA
<213> ORGANISM: Artificial Sequence
<220> FEATURE:
<223> OTHER INFORMATION: PCR-primer

<400> SEQUENCE: 42
ggacaaggac agattgtagc agttgctgat actgg                                  35

<210> SEQ ID NO 43
<211> LENGTH: 21
<212> TYPE: DNA
<213> ORGANISM: Artificial Sequence
<220> FEATURE:
<223> OTHER INFORMATION: PCR-primer

<400> SEQUENCE: 43
gcgattacag ttggggcaac c                                                 21

<210> SEQ ID NO 44
<211> LENGTH: 23
<212> TYPE: DNA
<213> ORGANISM: Artificial Sequence
<220> FEATURE:
<223> OTHER INFORMATION: PCR-primer

<400> SEQUENCE: 44
ggtagcacga cggcatcact aac                                               23
```

<210> SEQ ID NO 45
<211> LENGTH: 29
<212> TYPE: DNA
<213> ORGANISM: Artificial Sequence
<220> FEATURE:
<223> OTHER INFORMATION: PCR-primer

<400> SEQUENCE: 45
gagctccata atacataatt ttcaaactg                              29

<210> SEQ ID NO 46
<211> LENGTH: 26
<212> TYPE: DNA
<213> ORGANISM: Artificial Sequence
<220> FEATURE:
<223> OTHER INFORMATION: PCR-primer

<400> SEQUENCE: 46
gtcgacaacg taagatgaaa ccttag                                 26

<210> SEQ ID NO 47
<211> LENGTH: 25
<212> TYPE: DNA
<213> ORGANISM: Artificial Sequence
<220> FEATURE:
<223> OTHER INFORMATION: PCR-primer

<400> SEQUENCE: 47
gtcgaccgct cgctttccaa tctga                                  25

<210> SEQ ID NO 48
<211> LENGTH: 31
<212> TYPE: DNA
<213> ORGANISM: Artificial Sequence
<220> FEATURE:
<223> OTHER INFORMATION: PCR-primer

<400> SEQUENCE: 48
gaattcaata atttatacac tattctattg g                           31

<210> SEQ ID NO 49
<211> LENGTH: 26
<212> TYPE: DNA
<213> ORGANISM: Artificial Sequence
<220> FEATURE:
<223> OTHER INFORMATION: PCR-primer

<400> SEQUENCE: 49
gttaacttga aaacggtgc ttaatc                                  26

<210> SEQ ID NO 50
<211> LENGTH: 59
<212> TYPE: DNA
<213> ORGANISM: Artificial Sequence
<220> FEATURE:
<223> OTHER INFORMATION: PCR-primer

<400> SEQUENCE: 50
tggtactggc cttaagggcc gaatatttat acaatatcat gagctccaca ttgaaaggg    59

<210> SEQ ID NO 51
<211> LENGTH: 1140
<212> TYPE: DNA
<213> ORGANISM: Artificial Sequence
<220> FEATURE:
<223> OTHER INFORMATION: Synthetic sequence of pSJ7305 encoding the Savinase" signal peptide-10Rpro+mature protease

<400> SEQUENCE: 51

| | | |
|---|---|---|
| atgaaaaaac ctttgggaaa aatcgtagca agcactgcac ttcttattag cgttgcattt | 60 | |
| tcttcatcta ttgcaagcgc tgcaacaggt gcattaccgc aatcgcctac gccagaagca | 120 | |
| gacgcagtca gcatgcaaga ggctttgcaa agagaccttg acttgacaag cgctgaagca | 180 | |
| gaagaattgt tggctgcaca agatacagct tttgaggttg acgaagctgc agctgaagca | 240 | |
| gcaggtgatg catatggagg atctgtcttc gacacagaat cgcttgaatt aaccgtgctt | 300 | |
| gtaaccgacg cagcagctgt agaagcagtc gaagcaacgg gagctggaac ggagcttgta | 360 | |
| tcgtatggta tcgatggatt agatgaaatc gttcaggaat aaatgcagc tgatgcagtc | 420 | |
| ccgggtgtgg ttggttggta tccggatgtt gctggagata cagttgtcct tgaagtgctt | 480 | |
| gagggttctg gagcagatgt ttctggttta ttggcagatg ctggtgttga tgctagcgca | 540 | |
| gtagaagtaa cgacatcaga tcaacctgaa ttgtacgctg atattattgg aggactggca | 600 | |
| tacacgatgg gtggtagatg ttctgtggga tttgcagcaa ccaacgcagc tggacaacct | 660 | |
| ggtttcgtaa cggctggaca ctgtggtaga gtaggtacgc aggtcacaat tggtaacgga | 720 | |
| agaggagttt tgaacagtc cgtctttccg ggtaatgacg cagcatttgt tagaggaacg | 780 | |
| tcaaattta cattgacaaa ccttgttttcc aggtataaca ccggaggtta cgcaacagtt | 840 | |
| gctggtcata accaagcacc gattggttcg agcgtttgca ggtccggatc aacgacagga | 900 | |
| tggcattgtg gtacgattca ggcaaggggt cagagcgtct cttatcctga aggaacagta | 960 | |
| accaacatga caagaaccac agtctgtgca gaaccgggag actccggagg ttcttatatc | 1020 | |
| tcaggtacgc aagcacaggg tgtaacctcg ggtggttcgg gaaattgtag aacgggagga | 1080 | |
| actacttttt atcaagaagt cactccgatg gtcaattctt ggggagtaag acttagaaca | 1140 | |

<210> SEQ ID NO 52
<211> LENGTH: 64
<212> TYPE: DNA
<213> ORGANISM: Artificial Sequence
<220> FEATURE:
<223> OTHER INFORMATION: Primer 388968

<400> SEQUENCE: 52

| | |
|---|---|
| gactgaattc gagctctata aaaatgagga gggaaccgaa tgaaaaaacc tttgggaaaa | 60 |
| atcg | 64 |

<210> SEQ ID NO 53
<211> LENGTH: 38
<212> TYPE: DNA
<213> ORGANISM: Artificial Sequence
<220> FEATURE:
<223> OTHER INFORMATION: Primer 388969

<400> SEQUENCE: 53

| | |
|---|---|
| gactaagctt acgcgttatg ttctaagtct tactcccc | 38 |

<210> SEQ ID NO 54
<211> LENGTH: 39
<212> TYPE: DNA
<213> ORGANISM: Artificial Sequence
<220> FEATURE:
<223> OTHER INFORMATION: Primer 393822

<400> SEQUENCE: 54

| | |
|---|---|
| gactgaattc acgcgtgagc tctataaaaa tgaggaggg | 39 |

```
<210> SEQ ID NO 55
<211> LENGTH: 36
<212> TYPE: DNA
<213> ORGANISM: Artificial Sequence
<220> FEATURE:
<223> OTHER INFORMATION: Primer 393823

<400> SEQUENCE: 55
gactaagctt gctagcctaa tgtgttgtac ggagtc                        36
```

STABLY MAINTAINED MULTIPLE COPIES OF AT LEAST TWO ORF IN THE SAME ORIENTATION

CROSS-REFERENCE TO RELATED APPLICATIONS

This application is a continuation of U.S. application Ser. No. 11/571,091, filed Dec. 21, 2006, now abandoned, which is a 35 U.S.C. 371 national application of PCT/DK2005/000409, filed Jun. 20, 2005, which claims priority or the benefit under 35 U.S.C. 119 of Danish application no. PA 2004 00968 filed Jun. 21, 2004, Danish application no. PA 2004 01569 filed Oct. 13, 2004, U.S. provisional application No. 60/581,834 filed Jun. 21, 2004, and U.S. provisional application No. 60/618,487 filed Oct. 13, 2004. The contents of these applications are fully incorporated herein by reference.

REFERENCE TO A SEQUENCE LISTING

This application contains a Sequence Listing in computer readable form, which is incorporated herein by reference.

TECHNICAL FIELD

A method for constructing a stable cell expressing a gene of interest and comprising at least two copies of said gene on the chromosome.

BACKGROUND ART

In the industrial production of polypeptides it is of interest to achieve a product yield as high as possible and to be able to control the said expression. One way to increase the yield is to increase the copy number of a gene encoding a polypeptide of interest. This can be done by placing the gene on a high copy number plasmid. However, plasmids are unstable and are often lost from the host cells if there is no selective pressure during the cultivation of the host cells. Another way to increase the copy number of the gene of interest is to integrate it into the host cell chromosome in multiple copies. It has previously been described how to integrate a gene into the chromosome by double homologous recombination without using antibiotic markers (Hone et al., Microbial Pathogenesis, 1988, 5: 407-418); integration of two genes has also been described (Novo Nordisk: WO 91/09129 and WO 94/14968). A problem associated with integrating several copies of a gene into the chromosome of a host cell is instability of the multiple copies of the gene. Due to the sequence identity of the copies there is a high tendency for them to recombine and cross out of the chromosome during cultivation of the host cell unless a selective marker or other essential DNA is included between the copies, and selective pressure is applied during cultivation. This is especially true if the genes are located in relative close vicinity of each other. It has been described how to integrate two genes closely spaced in anti-parallel tandem to achieve better stability (Novo Nordisk: WO 99/41358).

In the above described solution to the stability problem each copy of the gene of interest requires its own promoter. In the case where several copies of a gene are integrated on the chromosome in different locations a variation in the level of expression might occur due to the different environment of the promoter. One way of obtaining high uniform levels of expression from multiple copies of a gene would be to transcribe all the copies from a polycistronic messenger controlled by one promoter region. This, however, would lead to the described instability of the construct.

It is therefore desirable to be able to integrate several copies of the same gene in close proximity to each other and being controlled by the same promoter in front of the first copy. Such a construct will normally be unstable when integrated on the chromosome due to the above described recombination taking place. It is therefore desirable to have alternative solutions to the stability problem experienced when having multiple copies of the same gene in close proximity on the host chromosome.

The present invention provides a solution in which at least two copies of the gene can be integrated in the same orientation on the host cell chromosome, either in different positions or in the same position e.g. as a tandem repeat.

SUMMARY OF THE INVENTION

It has now been found that at least two copies of the "same" gene can be stably integrated on the host cell chromosome in parallel tandem by introducing changes into the DNA sequence of at least one of the gene copies which does not change the amino acid sequence of the resulting protein encoded by the changed DNA sequence. In this way it is possible to have multiple copies of a gene wherein all the copies encode identical proteins having the same amino acid sequence but where the DNA sequences all are different compared to each other. The extent of the modification necessary in order to stabilize the multiple copies in parallel repeat may vary and will of course depend on the level of stability desired as well as on the host organism and growth conditions etc.

The first aspect of the present invention therefore relates to a method for constructing a host cell expressing a polypeptide of interest from at least two ORF's stably integrated onto the chromosome of the host cell comprising the steps of:

a) providing the at least two ORF's encoding the same polypeptide, wherein the at least two DNA sequences of the ORF's differ in at least one position;

b) integrating the at least two ORF's in the same orientation on the host cell chromosome.

The second aspect of the present invention relates to a host cell comprising at least two ORF's encoding the same polypeptide stably integrated in the same orientation onto the host cell chromosome wherein the at least two DNA sequences of the ORF's differ in at least one position.

The third aspect of the present invention relates to a nucleic acid construct comprising at least two ORF's encoding the same polypeptide in the same orientation, wherein the at least two DNA sequences of the ORF's differ in at least one position.

The fourth aspect of the present invention relates to a method of producing the same polypeptide from at least two ORF's stably integrated onto the host cell chromosome comprising the steps of:

i) culturing a host cell according to the invention under conditions conducive for the expression of the polypeptide; and optionally ii) recovering the polypeptide.

BRIEF DESCRIPTION OF THE DRAWING(S)

The invention is explained in detail below with reference to the drawing, in which FIG. 1 shows a nucleic acid construct of the invention in a vector, pSJ7365, suitable for integrating two ORF in tandem repeat on the chromosome of the host cell.

DETAILED DESCRIPTION OF THE INVENTION

The object of the present invention is to solve the observed instability problem associated with expression of multiple gene copies integrated on a host cell chromosome in the same orientation, from e.g. a polycistronic messenger, and at the same time reduce the time required for constructing the host cell. According to the present invention only integration in one location is necessary.

This object is solved by a method for constructing a host cell expressing a polypeptide of interest from at least two ORF's stably integrated onto the chromosome of the host cell comprising the steps of:
 a) providing the at least two ORF's encoding the same polypeptide, wherein the at least two DNA sequences of the ORF's differ in at least one position;
 b) integrating the at least two ORF's in the same orientation on the host cell chromosome.

An "open reading frame", (ORF), in the present invention means a DNA sequence that contains a signal for the start of translation followed in the correct register by a sufficient length of amino acid-encoding triplets to form a protein or a polypeptide, followed by a signal for termination of translation.

A "polypeptide" in the present invention means two or more amino acids linked by peptide bonds.

The "same polypeptide" referred to above is intended to mean that the at least two open reading frames (ORF's) encode functionally identical polypeptides. Therefore polypeptides having insignificant sequence differences, which do not alter the functionality of the polypeptide, e.g. in the case where an amino acid which does not alter the function has been changed or where additions or deletions have been introduced in the C- or N-terminus, are also comprised. In one particular embodiment the "same polypeptide" refers to identical polypeptides.

The ORF's according to the invention can be integrated at different positions on the host cell chromosome or at the same position. The instability problems observed is more pronounced when the ORF's are located close together, however, the method according to the invention should provide stability to multiple ORF's encoding the same polypeptide in any situation where such multiple copies are present on the chromosome or on a plasmid in the same orientation.

When the ORF's are integrated at different positions on the host cell chromosome it is necessary to provide a control sequence, e.g. a promoter, in front of each of the ORF's. This usually requires several constructs, one for each site of integration, or a construct that will result in random integration on the host cell chromosome. In any case such integration could result in a situation in which it is more difficult to obtain the desired expression level and the desired control of expression. It is therefore desirable to have a construct where the ORF's are controlled by a single control region in front of several copies of the ORF's encoding the same polypeptide. This makes construction and integration easier to perform. The resulting messenger transcribed from such a construct is known as a polycistronic messenger.

In one particular embodiment of the present invention therefore the ORF's are transcribed as a polycistronic messenger.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide.

The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook J, Fritsch E F, Maniatis T (1989) Molecular Cloning: a Laboratory Manual. ($2^{nd}$ edn), Cold Spring Harbor, N.Y.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

Preferred terminators for bacterial host cells, such as a *Bacillus* host cell, are the terminators from *Bacillus licheniformis* alpha-amylase gene (amyL), the *Bacillus stearothermophilus* maltogenic amylase gene (amyM), or the *Bacillus amyloliquefaciens* alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The nucleic acid construct according to the present invention is used in the method of the invention for the construction of the host cell.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as, e.g., ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The cell is preferably transformed with a vector comprising ORF's of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Particularly, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

After integration of the ORF's in the same orientation, e.g. at the same location on the host cell chromosome, the degree of instability will depend on the length of segments within the ORF's wherein the sequence identity is 100%. The minimal requirements for homologous recombination to occur, has been studied and varies among different organisms (Chédin et al., 1994, Mol. Microbiol., 12: 561-569; Ayares et al., 1986, Proc. Natl. Acad. Sci. 83, 5199-5203; Puchta and Hohn, 1991, Nucleic Acid Research 19:2693-2700; Khasanov et al., 1992, Mol. Gen. Genet. 234:494-497; Watt et al., 1985, Proc. Natl. Acad. Sci. 82:4768-4772), and ranges from about 400 bp to about 10 bp.

According to the invention it is not so much the number of changes but rather the spacing or distribution of the changes which will affect the stability. The purpose of the changes is to ensure that segments having a 100% sequence identity between the at least two ORF's at the most have a length of 1000 bp. The shorter the said length, the less frequent recombination will take place. In a particular embodiment the segment (contiguous sequence) having a 100% sequence homology is at the most 750 bp, particularly 500 bp, more particularly 250 bp, more particularly 200 bp, even more particularly 150 bp, most particularly 100 bp.

In a further embodiment of the invention the segment length is at the most 80 bp, particularly 70 bp, more particularly 50 bp, even more particularly 40 bp, more particularly 30 bp, or at the most 20 bp or 10 bp.

In one embodiment the ORF encodes a polypeptide corresponding to a complete protein. This could be a mature form of the protein or including the pro-peptide. In prokaryotes the situation is relatively simple since the DNA sequence comprising the ORF will be a contiguous DNA sequence not interrupted by non-coding regions. In Eukaryotes the situation is different and in this case the at least two ORF's could be represented by DNA sequences comprising both introns and exons. The essential feature according to the invention will, however, be unchanged since the stability of the construct relies on the introduction of sequence changes affecting the recombination frequency, whether present in coding or non-coding regions, which changes will not result in a different polypeptide but rather the same polypeptide will be produced.

The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

Host Cells

The present invention also relates to recombinant host cells, comprising an ORF of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus,* and *Enterococcus.* Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus,* or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus.*

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278). The host cell may be a eukaryote, such as a non-human animal cell, an insect cell, a plant cell, or a fungal cell. In one particular embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9,* 1980).

The yeast host cell may be a *Candida, Hansenula, Kluyveromyces, Pichia, Saccharomyces, Schizosaccharomyces,* or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium,* or *Trichoderma.*

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The invention relates to a recombinant host cell comprising a polynucleotide of the invention, or an expression vector or polynucleotide construct of the invention. In a preferred embodiment, the recombinant host cell is a *Bacillus* cell.

Plants

The present invention also relates to a transgenic plant, plant part, or plant cell which has been transformed with a nucleic acid sequence encoding a polypeptide so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor. In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *festuca, lolium,* temperate grass, such as *Agrostis,* and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.* Low-phytate plants as described e.g. in U.S. Pat. Nos. 5,689,054 and 6,111,168 are examples of engineered plants.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the protease in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, Bio/Technology 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

Enzymes Encoded by the ORF

The ORF's according to the invention encodes the same polypeptide, which in a particular embodiment is an enzyme.

The enzyme in the context of the present invention may be any enzyme obtainable by fermentation. The enzyme classification employed in the present specification and claims is in accordance with *Recommendations* (1992) *of the Nomenclature Committee of the International Union of Biochemistry and Molecular Biology*, Academic Press, Inc., 1992.

Accordingly the types of enzymes which may appropriately be expressed in the host cell of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1) such as haloperoxidase, laccases (EC 1.10.3.2) and glucose oxidases (EC 1.1.3.4)], while preferred transferases are transferases in any of the following sub-classes:

a) Transferases transferring one-carbon groups (EC 2.1);
b) Transferases transferring aldehyde or ketone residues (EC 2.2); acyltransferases (EC 2.3);
c) Glycosyltransferases (EC 2.4);
d) Transferases transferring alkyl or aryl groups, other than methyl groups (EC 2.5); and
e) Transferases transferring nitrogenous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases.

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at www.chem.gm-w.ac.uk/iubmb/enzyme/index.html).

Proteases are classified on the basis of their catalytic mechanism into the following groups: Serine proteases (S), Cysteine proteases (C), Aspartic proteases (A), Metalloproteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

Serine proteases are ubiquitous, being found in viruses, bacteria and eukaryotes; they include exopeptidase, endopeptidase, oligopeptidase and omega-peptidase activity. Over 20 families (denoted S1-S27) of serine proteases have been identified, these being grouped into 6 clans denoted SA, SB, SC, SE, SF, and SG, on the basis of structural similarity and functional evidence (Barrett et al. 1998. Handbook of proteolytic enzymes). Structures are known for at least four of the clans (SA, SB, SC and SE), these appear to be totally unrelated, suggesting at least four evolutionary origins of serine peptidases. Alpha-lytic endopeptidases belong to the chymotrypsin (SA) clan, within which they have been assigned to subfamily A of the S2 family (S2A).

Another classification system of proteolytic enzymes is based on sequence information, and is therefore used more often in the art of molecular biology; it is described in Rawlings, N. D. et al., 2002, MEROPS: The protease database. Nucleic Acids Res. 30:343-346. The MEROPS database is freely available electronically at www.merops.ac.uk. According to the MEROPS system, the proteolytic enzymes classified as S2A in 'The Handbook of Proteolytic Enzymes', are in MEROPS classified as 'S1E' proteases (Rawlings N D, Barrett A J. (1993) Evolutionary families of peptidases, Biochem. J. 290:205-218).

In particular embodiments, the proteases of the invention and for use according to the invention are selected from the group consisting of:
(a) proteases belonging to the EC 3.4.-.-.- enzyme group;
(b) Serine proteases belonging to the S group of the above Handbook;
(c1) Serine proteases of peptidase family 52A;
(c2) Serine proteases of peptidase family S1E as described in Biochem. J. 290:205-218 (1993) and in MEROPS a protease database, release 6.20, Mar. 24, 2003, (see for example, the website at www.merops.ac.uk). The database is described in Rawlings, N.D., O'Brien, E. A. & Barrett, A. J. (2002) *MEROPS*: the protease database. Nucleic Acids Res. 30, 343-346.

For determining whether a given protease is a Serine protease, and a family S2A protease, reference is made to the above Handbook and the principles indicated therein. Such determination can be carried out for all types of proteases, be it naturally occurring or wildtype proteases; or genetically engineered or synthetic proteases.

Accordingly in one particular embodiment of the invention the enzyme is a protease. In another particular embodiment, the protease is a serine protease. The serine protease is in one embodiment chosen from the group consisting of S2A or S1E. In a still further embodiment the serine protease is encoded from a sequence chosen from the group consisting of SEQ ID NO: 1, 2 or 51.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C.

Examples of protease substrates are casein, such as Azurine-Crosslinked Casein (AZCL-casein). For the purposes of this invention, the so-called pNA Assay is a preferred assay. S2A protease activity can be measured using the PNA assay with succinyl-alanine-alanine-proline-phenylalnine-paranitroanilide as a substrate unless otherwise mention. The principle of the PNA assay is described in Rothgeb, T. M., Goodlander, B. D., Garrison, P. H., and Smith, L. A., Journal of the American Oil Chemists' Society, Vol. 65 (5) pp. 806-810 (1988).

In the present context, the term "carbohydrase" is used to denote not only enzymes capable of breaking down carbohydrate chains (e.g. starches) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose α-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), arabinan endo-1,5-α-L-arabinosidases (3.2.1.99), lactases (3.2.1.108), chitosanases (3.2.1.132) and xylose isomerases (5.3.1.5).

Examples of commercially available oxidoreductases (EC 1.-.-.-) include Gluzyme™ (enzyme available from Novo Nordisk A/S).

Examples of commercially available proteases (peptidases) include Kannase™ Everlase™, Esperase™, Alcalase™, Neutrase™, Durazym™, Savinase™, Pyrase™, Pancreatic Trypsin NOVO (PTN), Bio-Feed™ Pro and ClearLens™ Pro (all available from Novo Nordisk A/S, Bagsvaerd, Denmark).

Other commercially available proteases include Maxatase™, Maxacal™ Maxapem™, Opticlean™ and Purafect™ (available from Genencor International Inc. or Gist-Brocades).

Examples of commercially available lipases include Lipoprime™ Lipolase™ Lipolase™ Ultra, Lipozyme™, Palatase™, Novozym™ 435 and Lecitase™ (all available from Novo Nordisk A/S). Other commercially available lipases include Lumafast™ (*Pseudomonas mendocina* lipase from Genencor International Inc.); Lipomax™ (*Pseudomonas pseudoalcaligenes* lipase from Gist-Brocades/Genencor Int. Inc.; and *Bacillus* sp. lipase from Solvay enzymes.

Examples of commercially available carbohydrases include Alpha-Gal™, Bio-Feed™ Alpha, Bio-Feed™ Beta, Bio-Feed™ Plus, Bio-Feed™ Plus, Novozyme™ 188, Celluclast™ Cellusoft™, Ceremyl™, Citrozym™, Denimax™, Dezyme™, Dextrozyme™, Finizym™ Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novo Nordisk A/S).

Combinations of enzymes may be obtained by fermenting two or more enzymes simultaneously in the same fermentation broth using this liquid or a processed liquid thereof as a starting material in a process of the invention. Alternatively combinations of enzymes may be obtained by fermenting the enzymes separately and using mixtures of different fermentation broths and/or processed liquids thereof as a starting material for the process of the invention.

Methods of Production

The present invention also relates to methods for producing a polypeptide of the present invention comprising (a) cultivating a host cell or a transgenic plant or animal under conditions conducive for production of the polypeptide in a supernatant; and optionally (b) recovering the polypeptide.

The present invention therefore relates to a method of producing the same polypeptide from at least two ORF's stably integrated onto the host cell chromosome comprising the steps of:

i) culturing a host cell according to the invention under conditions conducive for the expression of the polypeptide; and optionally ii) recovering the polypeptide.

The essential features of the invention will as discussed above also stabilize the at least two copies of an ORF encoding the same polypeptide when present on a plasmid, e.g. an expression vector.

In a further embodiment the present invention therefore relates to a method of producing the same polypeptide from at least two ORF's present on a plasmid comprising the steps of:

i) culturing a host cell comprising a plasmid comprising a nucleic acid construct of the invention under conditions conducive for the expression of the polypeptide; and optionally ii) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a product, or disappearance of a substrate. For example, a protease assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

EXAMPLES

Media.

LB agar, TY buillon medium and BPX shake flask medium have all been described in Patent Publication WO 94/14968.

PS-1 shake flask medium (10% sucrose, 4% soybean flour, 1% $Na_2SO_4.12H_2O$, 0.5% $CaCO_3$, and 0.01% pluronic acid) has been described in U.S. Pat. No. 6,255,076, example 28.

Example 1. Synthetic DNA Sequences Encoding Protease 10R

Protease 10R is a proteolytic enzyme produced by *Nocardiopsis prasina* NRLL 18262.

The DNA sequence given as SEQ ID NO: 1 is a synthetic DNA sequence encoding the signal peptide coding region from the *Bacillus clausii* alkaline protease gene, Savinase®, followed in frame by a synthetic DNA sequence encoding the pro+mature parts of the 10R protease. The synthetic DNA sequence is changed compared to the *Nocardiopsis* wildtype sequence, but it still encodes the wildtype 10R enzyme. A synthetic gene can be constructed by PCR assembly of overlapping oligonucleotides in various methods described eg. by Stemmer et al, Gene 164, pp-49-53, 1995; Dillon and Rossen, BioTechniques 9, 298-300, 1990; Prodromou and Pearl, Protein Engineering 5, 827-829, 1992; Chen et al., Journal of American Chemical Society 116, 8799-8800, 1994 and others.

Genes of the desired sequence can also be purchased from commercial companies like DNA2.0 inc., 1455 Adams Drive, Menlo Park, Calif. 94025.

The DNA sequence given as SEQ ID NO: 2 is a DNA sequence encoding the signal peptide coding region from the *Bacillus clausii* alkaline protease gene, Savinase®, followed in frame by a synthetic DNA sequence encoding the pro+mature parts of the 10R protease, followed in frame by an additional 6 basepair synthetic DNA sequence encoding the amino acid sequence TQ. The synthetic DNA sequence is changed compared to the *Nocardiopsis* wildtype sequence, and changed compared to SEQ ID NO: 1, but it still encodes the wildtype 10R enzyme, with an addition of the two amino acids TQ at the C-terminal. As above, this synthetic DNA segment could be obtained e.g. by PCR assembly of overlapping oligonucleotides in various methods described eg. by Stemmer et al, Gene 164, pp-49-53, 1995; Dillon and Rossen, BioTechniques 9, 298-300, 1990; Prodromou and Pearl, Protein Engineering 5, 827-829, 1992; Chen et al., Journal of American Chemical Society 116, 8799-8800, 1994 and others.

The DNA sequences given as SEQ ID NO's: 3-7 are DNA sequences encoding the signal peptide coding region from the *Bacillus clausii* alkaline protease gene, Savinase®, followed in frame by a synthetic DNA sequence encoding the pro+mature parts of the 10R protease. In the context of the present patent application, these DNA sequences can be regarded as examples of different DNA sequences encoding the same polypeptide product. It is not important, for the purpose of serving as an illustration of the present invention, that one sequence encodes a polypeptide which has a two amino acid C-terminal extension.

Example 2. Construction of Strain *Bacillus subtilis* ppP715-4, Containing a Chromosomally Integrated Copy of a Synthetic Gene Encoding the Protease 10R Enzyme The use of pDG268-derived plasmids for introduction of aprL expression cassettes into the amyE locus of *B. subtilis* in single copy has been described in details (Widner, B., Thomas, M., Sternberg, D., Lammon, D., Behr, R., and Sloma, A. (2000) Development of marker-free strains of *Bacillus subtilis* capable of secreting high levels of industrial enzymes. Journal of Industrial Microbiology & Biotechnology, 25, 204-212; Widner, W., Sloma, A., Thomas, M. D. (2003) Methods for producing a polypeptide in a *Bacillus* cell. United States Patent Application Publication US 2003/0170876 A1). FIG. 25 in patent application US 2003/0170876 specifically illustrates a plasmid containing a particular composite promoter, including the cryIIIA promoter and mRNA stabilizing region. This plasmid was used as a vector plasmid to make a construct, in which the segment between a PvuI site in the signal peptide coding region of the aprL gene (encoding Savinase®) and a MluI site present immediately downstream of the end of the aprL coding region was replaced by the PvuI-MluI part of a synthetic DNA fragment having the sequence given as SEQ ID NO: 8 (which has the PvuI site at pos.68-73, and the MluI site at the 3' end). A plasmid was thereby constructed, which contained a DNA sequence encoding the signal peptide coding region from the *Bacillus clausii* alkaline protease gene, Savinase®, followed in frame by a synthetic DNA sequence encoding the pro+mature parts of the 10R protease. This coding region was expressed using the composite consensus amyQ promoter/cryIIIA promoter/stabilizer, and it was integrated into the amyE locus of strain *B. subtilis* A164Δ5, as described in Widner et al. 2000, above. The resulting strain was named PP715-4.

Example 3. Construction of a Plasmid, pSJ6869, Carrying SEQUENCE ID NO: 1 Encoding Protease 10R pSJ5801

This is a pUC19 (Yanisch-Perron et al., 1985, *Gene* 33(1): 103-119) based plasmid carrying the transcriptional terminator from the *B. licheniformis* alpha-amylase gene, amyL. It was made by PCR amplification with:

```
Primer 1:
                                    (SEQ ID NO: 9)
5'-GACTCTGCAGCCGCGGACGCGTGCTAGCGGCCGCGTCGACTAGAAGA GCAGA-GAGGACGG-3'
and Primer 2:
                                    (SEQ ID NO: 10)
5'-GACTAAGCTTATCGATGATCAAGATCTCAACGAAATTTATAAGACGG

GC-3'
``` using chromosomal DNA of *B. licheniformis* as template, digestion of the PCR fragment with HindIII and PstI, and ligation into HindIII+PstI digested pUC19. The ligation mixture was transformed into *E. coli* SJ2 (Diderichsen et al., 1990, J. Bacteriol. 172(8): 4315-4321) by electroporation, selecting ampicillin resistance. 2 transformants, harbouring plasmids with the correct sequence of the PCR amplified terminator segment, were kept as SJ5801 (SJ2/pSJ5801) and SJ5802 (SJ2/pSJ5802).

pSJ6074 pSJ6074 is a pUC19 based plasmid carrying a segment consisting of the mRNA stabilizer sequence from the *B. thuringiensis* subsp. *tenebrionis* cryIIIA gene (a sequence found upstream of the coding region of the cryIIIA gene; Agaisse and Lereclus (1994) Mol. Microbiol. 13: 97-107), followed by the ribosome binding site from the *B. clausii* Savinase® gene, followed again by the Savinase® signal peptide coding sequence fused in-frame to a synthetic sequence coding for the *Nocardiopsis prasina* NRRL 18262 10R protease pro+mature regions, followed again by the amyL terminator. The cryIIIA stabilizer-10R construct was present as a chromosomally integrated segment in *B. subtilis* PP715-4, described in Example 2. Chromosomal DNA from PP715-4 was used as template in a PCR amplification, using a 61° C. annealing temperature, with primers

```
Primer 3:
                                    (SEQ ID NO: 11)
5'-AATTGGCGCCTGTCCAGACTGTCCGCTGTG-3'
and Primer 4:
                                    (SEQ ID NO: 12)
5'-GATTAACGCGTTATGTACGGAGTCTAACTCCCCAAG-3'
```

An aliquot of the PCR fragment from the above reaction was then used as template in a new PCR reaction (61° C. annealing temperature) with primers

```
Primer 5:
                                    (SEQ ID NO: 13)
5'-GACTGAATTCAGATCTAAAGATAATATCTTTGAATTGTAACG-3'
and Primer 6:
                                    (SEQ ID NO: 14)
5'-GACTGCTAGCACGCGTTATGTACGGAGTCTAAC-3'
```

A PCR fragment of the expected size was obtained, digested with EcoRI+MluI, and ligated to EcoRI+MluI digested pSJ5801. The ligation mixture was transformed into *E. coli* SJ2 by electroporation, selecting ampicillin resistance. 3 transformants with correctly sized inserts were DNA sequenced, and all contained errors in the PCR amplified segment. All had an error at position 38 relative to the first nucleotide of the EcoRI site (at this position the sequence TAACGCCCC changed to TAACCCCCC). One had another error in the first part of the sequence (pos. 98 relative to the first nucleotide of the EcoRI site, sequence ACCTTCTTC changed to ACCTACTTC) and was kept as SJ6065 (SJ2/pSJ6065), whereas another had an error in the last part of the sequence (10 nucleotides before the first nucleotide of the MluI site, AGACTCCGT changed to AGACGCCGT) and was kept as SJ6064 (SJ2/pSJ6064).

The 1.2 kb EcoRI-PstI fragment was excised from pSJ6064, ligated to the 3.2 kb PstI-EcoRI fragment of pSJ6065, and the ligation mixture transformed into *E. coli* SJ2 by electroporation, selecting ampicillin resistance. 3 plasmids with correct restriction pattern were DNA sequenced, and all found to have the DNA segments exchanged as desired. 2 were kept, SJ6074 (SJ2/pSJ6074) and SJ6075 (SJ2/pSJ6075). These plasmids contain a construct that still has an error at position 38 relative to the first nucleotide of the EcoRI site (TAACGCCCC changed to TAACCCCCC), but as this is close to the distal end of a 500 bp region that will eventually be used to direct homologous recombination with the host cell chromosome, and therefore with high probability will not become part of the final chromosomal construct, it was accepted.

pSJ6814 pSJ6814 is a pUC19 based plasmid with the same structure as pSJ6074, with the difference that the Savinase® signal peptide-10Rpro+mature coding region consists of another synthetic DNA fragment with a DNA sequence different from that of pSJ6074, but still encoding the same amino acid sequence as the gene on pSJ6074. The synthetic coding region has the sequence given as SEQ ID NO:1. DNA containing this synthetic coding region was used as template in a PCR amplification with primers Primer 7:
(SEQ ID NO: 15)
5'-GACTGAATTCGAGCTCTATAAAAATGAGGAGGGAACCGAATGAAAAA ACCGCTGG
< sav RBS >< start coding region GAAAAATTG-3'
and -continued Primer 8:
(SEQ ID NO: 16)
5'-GACTAAGCTTACGCGTTATGTTCTAAGTCTAACGCCC-3'
< end coding region The annealing temperature was ramped down from 62° C. to 52° C., then kept constant at 59° C. A correctly sized PCR fragment was obtained, digested with SacI+MluI, and ligated to the 3.3 kb MluI-SacI fragment of pSJ6074. The ligation mixture was transformed into *E. coli* SJ2 by electroporation. The PCR amplified region was DNA sequenced on 2 plasmids, that by restriction digests were found to contain the desired insert. 1 plasmid had the correct DNA sequence, and was kept in strain SJ6814 (SJ2/pSJ6814).

pSJ6869

Plasmid pSJ6869 is designed to allow integration of the SEQUENCE ID NO: 1 expression cassette into the chromosome of a *B. licheniformis* strain, that already contains a triple-promoter (the amyL4199/scBAN/cryIIIA triple tandem promoter) integrated at the amyL locus, by homologous recombination at the cryIIIA stabilizer and downstream amyL segments.

It was constructed by excision of the 1.8 kb EcoRI-HindIII fragment from pSJ6814, and ligation of this fragment to the 4.6 kb EcoRI-HindIII fragment of plasmid pSJ5487 (described below). The ligation mixture was transformed into *B. subtilis* PL1801 competent cells, selecting erythromycin resistance (2 microgram/ml) at 30° C. *B. subtilis* PL1801 is a derivative of *B. subtilis* DN1885 (Diderichsen et al., 1990, J. Bacteriol. 172(8): 4315-4321) with deletions in protease genes apr and npr. 4 protease-positive transformants, forming halos on plates supplemented with skimmed milk, were analysed by restriction digest, and found to be correct. 2 were kept, SJ6869 (PL1801/pSJ6869) and SJ6870 (PL1801/pSJ6870).

Plasmid pSJ5487, pSJ5488.

Plasmid pSJ5487 is an integration vector constructed to allow insertion of expression cassettes at the amyL position in the *B. licheniformis* chromosome. It has the temperature-sensitive plasmid replication functions of pE194, encodes erythromycin resistance, and contains the oriT region from pUB110 to allow its transfer by conjugation (U.S. Pat. No. 6,066,473). It contains a segment derived from the *B. licheniformis* chromosome immediately upstream from the amyL promoter region, followed by a segment derived from the *B. licheniformis* chromosome immediately downstream of the amyL open reading frame. This last segment was amplified by PCR from chromosomal *B. licheniformis* DNA, using the following primers and an annealing temperature at 55° C.:

Primer 9:
(SEQ ID NO: 17)
5'-GACTGAATTCAGATCTACGCGTCCATGGGCTAGCGCGGCCGCGTCGACAGGCCT- CTTTGATTACATTTTATAATTAATTTTAAC-3'
and Primer 10:
(SEQ ID NO: 18)
5'-GACTGAATTCATGCATAAACTGCATCCCTTACTTGTTTTTCGTGTGCCTATTTTTGTGA-

ATCGACGTCCCGAATACAACGACAC-3'

The PCR amplified fragment was digested with NsiI+BglII, and ligated to BglII+EcoRI+EcoRI+NsiI fragments of a pSJ2739 (U.S. Pat. No. 6,100,063) derived vector containing the upstream amyL segment. The ligation mixture was transformed into competent *B. subtilis* DN1885, selecting erythromycin resistance (5 microgram/ml) at 30° C. Two correct transformants were kept, as SJ5487 (DN1885/pSJ5487), and SJ5488 (DN1885/pSJ5488).

Example 4. Construction of a Plasmid, pSJ6996, Carrying Sequence ID No: 2, Encoding Protease 10R with a Two Amino Acid Extension pSJ6996 is a pUC19 based plasmid with the same structure as pSJ6074, with the difference that the Savinase® signal peptide-10Rpro+mature coding region was extended to encode a 10R protein with a two amino acid C-terminal extension. It was constructed by PCR amplification using pSJ6074 as template, and primers

```
Primer 11:
                                           (SEQ ID NO: 19)
5'-GACTGAATTCAGATCTAAAGATAATATCTTTGAATTGTAACG-3'
and Primer 12:
                                           (SEQ ID NO: 20)
5'-GACTAAGCTTACGCGTCTATTGTGTTGTACGGAGTCTAACTCCCCA-
3'
```

The PCR amplified DNA fragment was digested with KpnI+MluI, and the 0.2 kb fragment ligated to the large MluI-KpnI fragment of pSJ6074. The ligation mixture was transformed into *E. coli* SJ2 by electroporation. Two transformants having the correct DNA sequence of the PCR amplified region were kept as SJ6996 (SJ2/pSJ6996) and SJ6997 (SJ2/pSJ6997).

Example 5. Construction of a Plasmid, pSJ7365, Carrying SEQUENCE ID NO: 1, Encoding Protease 10R, Followed by SEQUENCE ID NO: 2, Encoding Protease 10R with a Two Amino Acid Extension In order to insert desired restriction sites around the segment carrying SEQ ID NO: 2, pSJ6996 was used as template in a PCR amplification with primers

```
Primer 13:
                                           (SEQ ID NO: 21)
5'-GACTGAATTCACGCGTGAGCTCTATAAAAATGAGGAGGG-3'
and Primer 14:
                                           (SEQ ID NO: 22)
5'-GACTAAGCTTGCTAGCCTAATGTGTTGTACGGAGTC-3'
```

The PCR amplified DNA fragment was digested with EcoRI+HindIII, and ligated to the large HindIII-EcoRI fragment of pUC19. The ligation mixture was transformed into *E. coli* SJ2 by electroporation. Two transformants having an almost correct DNA sequence of the PCR amplified region were kept as SJ7351 (SJ2/pSJ7351) and SJ7352 (SJ2/pSJ7352). By mistake, one primer was erroneous and introduced a mutation which changed the two amino acid extension of the encoded protein from TQ to TH. This could, however, later be corrected by further cloning.

A segment of pSJ7351 containing the protease 10R-TH encoding open reading frame was subsequently inserted into plasmid pSJ6869, which already contained the protease 10R encoding open reading frame given in SEQUENCE ID NO: 1. The 1.2 kb MluI-NheI fragment of pSJ7351 was isolated, and inserted into the 6.5 kb NheI-MluI fragment of pSJ6869. The ligation mixture was transformed into *B. subtilis* PL1801 competent cells, selecting erythromycin resistance (2 microgram/ml) at 30° C. Two transformants were kept, SJ7355 (PL1801/pSJ7355) and SJ7356 (PL1801/pSJ7356).

Interestingly, plasmid DNA prepared from these strains revealed no sign of recombination between the tandemly arranged, parallel open reading frames encoding essentially identical enzymes, but differing in their DNA sequence. It is of particular interest, given that the vector plasmid is based on pE194, which is a rolling circle replicating plasmid of the kind on which tandem repeats are notoriously unstable (Gruss and Ehrlich, 1989, Microbiological reviews, 53(2), 231-241).

The desired construct should contain SEQUENCE ID NO: 2, encoding a 10R protein with the TQ amino acid extension. This was achieved by isolation of the 0.6 kb SacII-NheI fragment from plasmid pSJ6996, and ligation of this fragment to the 7.1 kb NheI-SacII fragment of pSJ7355. Transformants of *B. subtilis* PL1801 competent cells were selected using erythromycin resistance (2 microgram/ml) at 30° C. Two transformants were kept, SJ7365 (PL1801/pSJ7365) and SJ7366 (PL1801/pSJ7366).

Example 6. Construction of a *Bacillus licheniformis* Host Strain, Containing Two Triple-Promoters in its Chromosome Construction of *Bacillus licheniformis* MaTa2 Harbouring the P11 Promoter/amyL Expression Cassette in the amyL Locus The P11 promoter (U.S. Pat. No. 6,255,076; $Pr_{short\ "consensus"\ amyQ}/Pr_{crIIIA\ stab}$) was introduced upstream of the alpha-amylase gene amyL in *Bacillus licheniformis* SJ1904 (U.S. Pat. No. 5,733,753) by standard gene replacement procedures. Because of difficulties working with plasmids bearing fragments of the amyL coding region located downstream of functional promoters, the construction was performed in two steps. First the amyL promoter and amyL ribosome-binding site (RBS) were replaced with a composite promoter lacking the RBS (to prevent expression of amyL). A second gene replacement was then performed to reintroduce the RBS, thereby generating a functional expression cassette.

The pE194-based, temperature-sensitive plasmid pMRT064.1 (WO 03/054163) was introduced into *Bacillus licheniformis* strain SJ1904 via electroporation (Xue et. al., 1999, *Journal of Microbiological Methods* 34: 183-191). The cells were plated onto TBAB-agar plates supplemented with 1 μg of erythromycin and 25 μg of lincomycin per ml after incubation at 28° C. for 24-48 hours. An erythromycin-resistant transformant was isolated and grown in the presence of erythromycin (5 μg/ml) at the non-permissive temperature of 50° C. At this temperature, the pE194 origin of replication is inactive. Cells were able to grow in the presence of erythromycin only by integration of the plasmid into the amyL locus on the bacterial chromosome. To promote excision of the plasmid, which would result in the replacement of the endogenous amyL promoter with the P11 promoter and the subsequent loss of the RBS, the integrants were grown in Luria-Bertani (LB) medium without selection at the permissive temperature of 30° C. for several generations. At this temperature the pE194 origin of replication was active and promoted excision of the plasmid from the genome (Molecular Biological Methods for *Bacillus*, edited by C. R. Harwood and S. M. Cutting, 1990, John Wiley and Sons Ltd.). The cells were then plated on non-selective LB agar plates and colonies which contained the desired promoter replacement and loss of the pE194-based replicon were identified by the following criteria: (1) the inability to form haloes on Tryptose blood agar base (TBAB) plates containing a 0.5% starch-azure (Sigma Chemical Co., St.

Louis, Mo.) plus TBAB overlay indicated the presence of the P11 promoter and the loss of the amyL RBS; and (2) erythromycin sensitivity indicated the loss of the pE194-based replicon. One transformant was chosen which met these three criteria and designated *Bacillus licheniformis* SJ 1904::pMRT064.1.

The amyL RBS was restored in the above strain as follows. Plasmid pNBT23 (pDG268MCSΔNeo-Pr$_{short\ "consensus"\ amyQ}$/Pr$_{cryIIIA}$/CryIIIAstab/SAV, U.S. Pat. No. 6,255,076) was digested with PacI, the ends were blunted with T4 DNA polymerase I (Roche Applied Science; Indianapolis, Ind.), and then digested with SalI. Plasmid pUC19 (Yanisch-Perron et al., 1985, *Gene* 33(1): 103-119) was digested with Ecl136II and SalI. The digestions were resolved on a 0.8% agarose gel using 44 mM Tris Base, 44 mM boric acid, 0.5 mM EDTA buffer (0.5×TBE) buffer and the larger vector fragment (approximately 2661 bp) from pUC19 and the smaller cryIIIAstab/aprH 5' fragment (approximately 1069 bp) from pNBT23 were gel-purified using a QIAquick DNA Extraction Kit according to the manufacturer's instructions (QIAGEN, Valencia, Calif.). The two purified fragments were ligated together with T4 DNA ligase according to the manufacturer's instructions (Roche Applied Science; Indianapolis, Ind.) and the ligation mix was transformed into *E. coli* SURE® competent cells (Stratagene, Inc., La Jolla, Calif.). Transformants were selected on 2× yeast-tryptone (2×YT) agar plates supplemented with 100 μg of ampicillin per ml. Plasmid DNA was purified from several transformants using a Bio Robot 9600 according to the manufacturer's instructions (QIAGEN, Valencia, Calif.) and analyzed by EcoRI plus SalI digestion on a 0.8% agarose gel using 0.5×TBE buffer. The correct plasmid was identified by the presence of an approximately 1071 bp EcoRI/Sa/I cryIIIAstab/aprH 5' fragment and was designated pNBT28.

Plasmid pMRT038 was constructed by SOE (splicing by overlap extension) according to the procedure of Horton et al., 1989, *Gene* 77: 61-8. The amyL promoter region and 5' coding sequence from plasmid pDN1981 (U.S. Pat. No. 5,698,415) were PCR amplified using primers pairs 733-45-1 and 733-45-2, and 733-68-1 and 733-70-1, respectively, as shown below. PCR amplification was conducted in 50 μl reactions composed of 1 ng of pDN1981 DNA, 0.4 μM of each primer, 200 μM each of dATP, dCTP, dGTP, and dTTP, 1×PCR Buffer II (Applied Biosystems, Inc., Foster City, Calif.) with 2.5 mM MgCl$_2$, and 2.5 units of AmpliTaq Gold™ DNA polymerase (Applied Biosystems, Inc., Foster City, Calif.). The reactions were performed in a RoboCycler 40 thermacycler (Stratagene, Inc., La Jolla, Calif.) programmed for 1 cycle at 95° C. for 10 minutes; 25 cycles each at 95° C. for 1 minute, 50° C. for 1 minute, and 72° C. for 1 minute; and 1 cycle at 72° C. for 7 minutes. The PCR product was visualized using a 0.8% agarose-0.5×TBE gel. The expected fragments were approximately 600 and 500 bp, respectively. The final SOE fragment was amplified using primers 733-45-1 and 733-70-1 shown below. The final SOE fragment was cloned into pCR2.1 vector using the TA-TOPO Cloning Kit (Stratagene, Inc., La Jolla, Calif.). Transformants were selected on 2×YT agar plates supplemented with 100 μg of ampicillin per ml and incubated at 37° C. for 16 hours. Transformants carrying the correct plasmid were verified by DNA sequencing using M13 forward and reverse primers (Invitrogen, Inc, Carlsbad, Calif.). This plasmid was designated pMRT038.

Primer 733-45-1:
(SEQ ID NO: 23)
5'-GTCCTTCTTGGTACCTGGAAGCAGAGC-3'

Primer 733-45-2:
(SEQ ID NO: 24)
5'-GTATAAATATTCGGCCCTTAAGGCCAGTACCATTTTCCC-3'

Primer 733-68-1:
(SEQ ID NO: 25)
5'-TGGTACTGGCCTTAAGGGCCGAATATTTATACAATATCATGAGCTCC
ACATTGAAA-GGG-3'

Primer 733-70-1:
(SEQ ID NO: 26)
5'-GGTGTTCTCTAGAGCGGCCGCGGTTGCGGTCAGC-3'

Plasmid pNBT28 was digested with BglII, the ends were blunted with Klenow fragment, and then digested with SacI. Plasmid pMRT038 was digested with EcoRI, the ends were blunted with Klenow fragment, and then digested with SacI. The digestions were resolved on a 0.8% agarose gel using 0.5×TBE buffer and the larger vector fragment (approximately 3253 bp) from pNBT28 and the smaller fragment (approximately 593 bp) from pMRT038 were gel-purified using a QIAquick DNA Extraction Kit according to the manufacturer's instructions. The two purified fragments were ligated together with T4 DNA ligase and the ligation mix was transformed into *E. coli* SURE® competent cells. Transformants were selected on 2×YT agar plates supplemented with 100 μg of ampicillin per ml. Plasmid DNA was purified from several transformants using a QIAGEN Bio Robot 9600 according to the manufacturer's instructions and analyzed by EcoRI plus HindIII digestion on a 0.8% agarose gel using 0.5×TBE buffer. The correct plasmid was identified by the presence of an approximately 1168 bp EcoRI/HindIII fragment and was designated pNBT29.

Plasmids pNBT29 and pCJ791 (WO 03/054163) were digested with EcoRI and HindIII. The digestions were resolved on a 0.8% agarose gel using 0.5×TBE buffer and the larger vector fragment (approximately 4340 bp) from pCJ791 and the smaller fragment (approximately 1168 bp) from pNBT29 were gel-purified using a QIAquick DNA Extraction Kit according to the manufacturer's instructions. The two purified fragments were ligated together with T4 DNA ligase and the ligation mix was transformed into *Bacillus subtilis* 168Δ4 (WO 03/054163). Plasmid DNA was purified from several transformants using a QIAGEN tip-20 columns (QIAGEN, Inc., Valencia, Calif.) according to the manufacturer's instructions and analyzed by EcoRI plus HindIII digestion on a 0.8% agarose gel using 0.5×TBE buffer. The correct plasmid was identified by the presence of an approximately 1168 bp EcoRI/HindIII fragment and was designated pWWi001.1.

In order to restore the amyL RBS in *Bacillus licheniformis* strain SJ1904::pMRT064.1, plasmid pWWi001.1 was introduced into this strain via electroporation, then integrated into the chromosome and excised as described above, creating *Bacillus licheniformis* MaTa2. The desired clone was identified by the restoration of amyL expression which was assayed by growing the strain on TBAB plates containing a 0.5% starch-azure plus TBAB overlay. Strains producing amylase formed a clear halo around the colony or patch.

Construction of *Bacillus licheniformis* MaTa3 Harbouring the P12 Promoter/amyL Expression Cassette in the Native amyL Locus Plasmid pMRT064.1 was digested with HindIII, filled-in with Klenow fragment, and then digested with SfiI. Plasmid pNBT23 (pDG268MCSΔNeo-Pr$_{short\ "consensus"\ amyQ}$/Pr$_{cryIIIA}$/cryIIIAstab/SAV, U.S. Pat. No. 6,255,076) was digested with SfiI and Ecl136II. The digestions were resolved on a 0.8% agarose gel using 0.5×TBE buffer and the larger vector fragment (approximately 4892 bp) from pMRT064.1 and the smaller fragment (approximately 728 bp) from pNBT23 were gel-purified using a QIAquick DNA Extraction Kit according to the manufacturer's instructions. The two purified fragments were ligated together with T4 DNA ligase and the ligation mix was transformed into *Bacillus subtilis* 168Δ4. Plasmid DNA was purified from several transformants using QIAGEN tip-20 columns according to the manufacturer's instructions and analyzed by EcoRI plus HindIII digestion on a 0.8% agarose gel using 0.5×TBE buffer. The correct plasmid was verified by restriction enzyme and/or PCR analysis and was designated pWWi005.

Plasmid pWWi005 was introduced into *Bacillus licheniformis* MaTa2 via electroporation, then integrated and excised from the chromosome as described previously, replacing the P11 promoter with the P12 promoter (U.S. Pat. No. 6,255,076; Pr$_{short\ "consensus"\ amyQ}$/Pr$_{cryIIIA}$/cryIIIAstab), to create *Bacillus licheniformis* strain MaTa3. The expected fragment was approximately 230 bp.

```
Primer 961197:
                                        (SEQ ID NO: 27)
5'-GGCCTTAAGGGCCTGCTGTCCAGACTGTCCGCT-3'

Primer 94-935:
                                        (SEQ ID NO: 28)
5'-GGCGTTACAATTCAAAGA-3'-
```

Construction of amyL4199 (P6) Composite Promoters

The amyL4199 promoter (Pr$_{amyL4199}$, U.S. Pat. No. 6,100,063), hereafter designated the P6 promoter), was PCR-amplified from *Bacillus licheniformis* SJ1904 (U.S. Pat. No. 5,733,753) genomic DNA obtained according to the method of Pitcher et. al., 1989, supra, using the primers shown below, which incorporate a SfiI site and a SacI site, respectively.

```
Primer 950872:
                                        (SEQ ID NO: 29)
5'-CCAGGCCTTAAGGGCCGCATGCGTCCTTCTTTGTGCT-3'

Primer 991151:
                                        (SEQ ID NO: 30)
5'-GAGCTCCTTTCAATGTGATACATATGA-3'
```

PCR amplifications were conducted in triplicate in 50 μl reactions composed of 50 ng of chromosomal DNA, 0.4 μM each of primers 950872 and 991151, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 9 minutes; 30 cycles each at 95° C. for 1 minute, 55° C. for 1 minute, and 72° C. for 1 minute; and 1 cycle at 72° C. for 5 minutes. The PCR product was visualized using a 0.8% agarose gel with 0.5×TBE buffer. The expected fragment was approximately 600 bp.

The 600 bp PCR fragment was cloned into pCR2.1 using the TA-TOPO Cloning Kit and transformed into *E. coli* OneShot™ competent cells according to the manufacturer's instructions (Stratagene, Inc., La Jolla, Calif.). Transformants were selected at 37° C. after 16 hours of growth on 2×YT agar plates supplemented with 100 g of ampicillin per ml. Plasmid DNA from these transformants was purified using a QIAGEN Bio Robot 9600 according to the manufacturer's instructions and analyzed by digestion with EcoRI and electrophoresis on a 0.8% agarose gel using 0.5×TBE buffer. The plasmid was found to have the correct expected fragments (approximately 3913 bp and 640 bp). The DNA sequence of the insert DNA was confirmed by DNA sequencing using M13 (−20) forward and M13 reverse primers (Invitrogen, Inc, Carlsbad, Calif.). A plasmid with the correct cloned sequence was designated pNBT30.

Plasmids pNBT3 (pDG268MCSΔNeo-Pr$_{cryIIIA}$/cryIIIAstab/SAV, U.S. Pat. No. 6,255,076) and pNBT30 were digested with SfiI and SacI. The digestions were resolved on a 0.8% agarose gel using 0.5×TBE buffer and the larger vector fragment (approximately 7931 bp) from pNBT3 and the smaller fragment (approximately 611 bp) from pNBT30 were gel-purified using a QIAquick DNA Extraction Kit according to the manufacturer's instructions. The two purified fragments were ligated together with T4 DNA ligase and the ligation mix was transformed into *E. coli* SURE® competent cells. Transformants were selected on 2×YT agar plates supplemented with 100 μg of ampicillin per ml. Plasmid DNA from these transformants was purified using a QIAGEN Bio Robot 9600 (QIAGEN, Valencia, Calif.) according to the manufacturer's instructions and analyzed by digestion with NcoI and electrophoresis on a 0.8% agarose gel using 0.5×TBE buffer. The plasmid was found to have the correct expected fragments (approximately 6802 bp and 1741 bp) and was designated pNBT31.

A Pr$_{amyL4199}$/Pr$_{cryIIIA}$/cryIIIAstab tandem promoter (P15) was constructed as follows. Plasmid pNBT2 (pDG268MCSΔ-Pr$_{cryIIIA}$/cryIIIAstab/SAV, U.S. Pat. No. 6,255,076) was digested with SfiI, the ends were blunted with T4 DNA polymerase, and then digested with Asp718. Plasmid pNBT31 was digested with Ecl136II and Asp718. The digestions were resolved on a 0.8% agarose gel using 0.5×TBE buffer and the larger vector fragment (approximately 8170 bp) from pNBT31 and the smaller fragment (approximately 996 bp) from pNBT2 were gel-purified using a QIAquick DNA Extraction Kit according to the manufacturer's instructions. The two purified fragments were ligated together with T4 DNA ligase and the ligation mix was transformed into *E. coli* SURE® competent cells. Transformants were selected on 2×YT agar plates supplemented with 100 μg of ampicillin per ml. Plasmid DNA was purified from several transformants using a QIAGEN Bio Robot 9600 according to the manufacturer's instructions and analyzed by SfiI plus SacI digestion on a 0.8% agarose gel using 0.5×TBE buffer. The correct plasmid was identified by the presence of an approximately 1235 bp fragment and was designated pNBT32.

A Pr$_{amyL4199}$/Pr$_{short\ "consensus"\ amyQ}$/cryIIIAstab composite promoter (P16) was constructed as follows. Plasmid pNBT31 was digested with DraIII and Ecl136II. Plasmid pNBT24 (PDG268MCSΔNeo-Pr$_{short\ consensus\ amyQ}$/long cryIIIAstab/SAV, U.S. Pat. No. 6,255,076) was digested with SfiI, the ends were blunted using T4 DNA polymerase I, and then digested with DraIII. The digestions were resolved on a 0.8% agarose gel using 0.5×TBE buffer and the larger vector fragment from pNBT31 and the smaller promoter fragment (approximately 1100 bp) from pNBT24 were gel-purified using a QIAquick DNA Extraction Kit according to the manufacturer's instructions. The two purified fragments were ligated together with T4 DNA ligase and the ligation mix was transformed into *E. coli* SURE® competent cells. Transformants were selected on 2×YT agar plates supplemented with 100 μg of ampicillin per ml.

Plasmid DNA was purified from several transformants using a QIAGEN Bio Robot 9600 according to the manufacturer's instructions and analyzed by SfiI plus SacI digestion on a 0.8% agarose gel using 0.5×TBE buffer. The correct plasmid was identified by the presence of an approximately 1400 bp SfiI/SacI fragment and was designated pNBT33.

Construction of *Bacillus licheniformis* MDT217, which Harbors the P17 Promoter/amyL Expression Cassette in the Native amyL Locus Plasmid pNBT33 was digested with AvaII and Ecl136II. Plasmid pMRT074 (WO 03/054163) was digested with NotI, the ends were flushed using T4 DNA polymerase, and then digested with AvaII. The digestions were resolved on a 0.8% agarose gel using 0.5×TBE buffer and the larger vector fragment (approximately 4433 bp) from pMRT074 and the smaller fragment (approximately 1157 bp) from pNBT33 were gel-purified using a QIAquick DNA Extraction Kit according to the manufacturer's instructions. The two purified fragments were ligated together with T4 DNA ligase and the ligation mix was transformed into *Bacillus subtilis* 168Δ4. Transformants were selected on TBAB-agar plates supplemented with 1 μg of erythromycin and 25 μg of lincomycin per ml after incubation at 28° C. for 24-48 hours. Plasmid DNA from several transformants was isolated using QIAGEN tip-20 columns according to the manufacturer's instructions and verified by digestion with BamHI plus Hind III. The resulting plasmid was designated pMDT006.

Plasmid pMDT006 was introduced into *Bacillus licheniformis* MaTa3 via electroporation. An erythromycin resistant transformant was isolated and the plasmid was integrated and excised from the chromosome as described previously. This resulted in the replacement of the P12 tandem promoter with the P16 promoter yielding *Bacillus licheniformis* strain MDT216. The desired clone was identified by PCR analysis using primers

```
                                    (SEQ ID NO: 28)
Primer 94-935: 5'-GGCGTTACAATTCAAAGA-3'-
and (SEQ ID NO: 31)
Primer 94-919: 5'-GGAAGTACAAAAATAAGC-3'
```

Plasmid pWWi005 was digested with SfiI and EcoRI to remove the DNA sequence located upstream of the amyL gene. The ends were blunted with T4 DNA polymerase and the fragments were resolved on a 0.8% agarose gel using 0.5×TBE buffer. The larger vector fragment (approximately 5069 bp) was gel-purified using a QIAquick DNA Extraction Kit according to the manufacturer's instructions. The purified fragment was ligated together with T4 DNA ligase and the ligation mix was transformed into *Bacillus subtilis* 168Δ4. Transformants were selected on TBAB-agar plates supplemented with 1 μg of erythromycin and 25 μg of lincomycin per ml after incubation at 28° C. for 24-48 hours. Plasmid DNA from several transformants was isolated using QIAGEN tip-20 columns according to the manufacturer's instructions and verified by digestion with BamHI plus HindIII. The resulting plasmid was designated pMDT007.

Plasmid pMDT007 was introduced into *Bacillus licheniformis* MDT216 via electroporation. An erythromycin-resistant transformant was isolated and the plasmid was integrated and excised from the chromosome as described previously, which resulted in the conversion of the P16 promoter to the PramyL4199/Prshort "consensus" amyQ/PrcryIIIA/cryIIIAstab triple tandem promoter (P17) yielding *Bacillus licheniformis* strain MDT217. The desired clone was identified by PCR analysis using primers 94-935 and 94-919 (above).

Construction of *Bacillus licheniformis* MDT220, a C-Component Protease-Deleted Strain

*Bacillus licheniformis* MDT220, a C-component-negative strain containing the amyL gene (accession no. M13256) under control of the P17 triple tandem promoter was constructed by deletion of the C-component gene of *Bacillus licheniformis* MDT217 as described below. A deleted version of the gene encoding *Bacillus licheniformis* C-component protease (U.S. Pat. No. 5,459,064, accession no. D10060, Kakudo et al., 1992, *J. Biol. Chem.* 267: 23782) was constructed by PCR using splicing by overlap extension (SOE) (Horton et al., 1989, supra). The 5' and 3' regions of the C-component gene were PCR amplified from *Bacillus licheniformis* SJ1904 DNA using primer 991173 (which introduced a 5' EcoRI restriction site) and primer 991174 for the 5' C-component fragment and primers 991175 and 991176 (which introduced a 3' HindIII restriction site) for the 3' C-component fragment, shown below.

```
Primer 991173:
                                    (SEQ ID NO: 32)
5'-GAATTCGACGGCTTCCCGTGCGCC-3'

Primer 991174:
                                    (SEQ ID NO: 33)
5'-GCAAGCGAGCACGGATTGTAAGTACAAGTTAGATA-3'

Primer 991175:
                                    (SEQ ID NO: 34)
5'-AACTTGTACTTACAATCCGTGCTCGCTTGCCGTAC-3'

Primer 991176:
                                    (SEQ ID NO: 35)
5'-AAGCTTCCATTCAAACCTGGTGAGGAAG-3'
```

PCR amplifications were carried out in triplicate in 30 μl reactions composed of 50 ng of chromosomal DNA, 0.4 μM each of primer pair 991173 and 991174 for the 5' C-component fragment or primer pair 991175 and 991176 for the 3' C-component fragment, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 9 minutes; 3 cycles each at 95° C. for 1 minute, 52° C. for 1 minute, and 72° C. for 1 minute; 27 cycles each at 95° C. for 1 minute, 55° C. for 1 minute, and 72° C. for 1 minute; and 1 cycle at 72° C. for 5 minutes. The PCR products were visualized using a 0.8% agarose-0.5×TBE gel. The expected fragments were approximately 290 bp in size. The final SOE fragment was generated using primer pair 991173 and 991176 according to Horton et al., 1989, supra, and cloned into pCR2.1 vector using the TA-TOPO Cloning Kit. Transformants were selected on 2×YT agar plates supplemented with 100 μg of ampicillin per ml after incubation at 37° C. for 16 hours. Plasmid DNA from several transformants was isolated using QIAGEN tip-20 columns according to the manufacturer's instructions and verified by DNA sequencing with M13 (−20) forward and M13 reverse primers. The plasmid harboring the SOE fragment was designated pNBT37.

Plasmids pCJ791 (WO 03/054163) and pNBT37 were digested with EcoRI and HindIII. The digestions were resolved on a 0.8% agarose gel using 0.5×TBE buffer and the larger vector fragment (approximately 4340 bp) from pCJ791 and the smaller C-component deletion fragment (approximately 580 bp) from pNBT37 were gel-purified using a QIAquick DNA Extraction Kit according to the manufacturer's instructions. The two purified fragments were ligated together with T4 DNA ligase and the ligation mix was transformed into *Bacillus subtilis* 168Δ4. Transformants were selected on TBAB-agar plates supplemented with 1 μg of erythromycin and 25 μg of lincomycin per ml after incubation at 28° C. for 24-48 hours. Plasmid DNA from several transformants was isolated using QIAGEN tip-20 columns according to the manufacturer's instructions and verified by digestion with EcoRI plus HindIII and agarose gel electrophoresis. A plasmid was identified, which yielded the expected fragment sizes of approximately 4340 bp and approximately 580 bp; and was designated pWWi002.

Plasmid pWWi002 was introduced into *Bacillus licheniformis* MDT217 via electroporation. An erythromycin resistant transformant was isolated and the plasmid was integrated and excised from the chromosome as described previously. Chromosomal DNA was isolated from several transformants according to Pitcher et al., 1989, supra, and was analyzed by PCR using primers 991173 and 991176 above to identify the C-component-deleted strains. Several transformants were identified which yielded the expected size PCR fragment of approximately 580 bp which confirmed a partial deletion of the C-component gene. One of these strains was chosen and designated *Bacillus licheniformis* MDT220.

Construction of *Bacillus licheniformis* Strain TH3 Containing One-Copy of the P17 Promoter/JP170 Expression Cassette in the amyL Locus Plasmid pMRT077 was constructed as follows. The upstream region and the 3' region of the amyL gene were fused via SOE using primer pair 733-45-1 and 733-45-7 and primer pair 757-19-1 and 733-45-6, respectively, shown below.

```
Primer 733-45-1:
                                    (SEQ ID NO: 23)
5'-GTCCTTCTTGGTACCTGGAAGCAGAGC-3'

Primer 733-45-7:
                                    (SEQ ID NO: 36)
5'-CATGCTGGGCCCTTAAGGCCAGTACCATTTTCCC-3'

Primer 757-19-1:
                                    (SEQ ID NO: 37)
5'-CAGTAGGCCTTAAGGGCCCAGCATGATTGAGCTCACCACCATGGG-

ATCCGCGGCCGCACAAGGGAAGGC-3'

Primer 733-45-6:
                                    (SEQ ID NO: 38)
5'-CAATTCATCCTCTAGAGTCTCAGG-3'
```

PCR amplification was conducted in 50 μl reactions composed of 1 ng of pDN1981 DNA (U.S. Pat. No. 5,698,415), 0.4 μM of each primer, 200 μM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 10 minutes; 25 cycles each at 95° C. for 1 minute, 50° C. for 1 minute, and 72° C. for 1 minute; and 1 cycle at 72° C. for 7 minutes. The PCR products were visualized in a 0.8% agarose gel using 0.5× TBE buffer. The expected fragments were approximately 600 and 500 bp, respectively. The final fragment was amplified using primers 733-45-1 and 733-45-6. The final fragment was cloned into pCR2.1 vector using the TA-TOPO Cloning Kit. Transformants were selected on 2×YT agar plates supplemented with 100 μg of ampicillin per ml and incubated at 37° C. for 16 hours. Transformants carrying the correct plasmid were verified by DNA sequencing using M13 forward and reverse primers. This plasmid was designated pMRT040.

Plasmid pMRT040 was digested with KpnI/XbaI, filled with Klenow fragment DNA polymerase in the presence of dNTPs, and a fragment of approximately 1000 bp was isolated from a 0.8% agarose-0.5×TBE gel using a QIAquick DNA purification Kit according to the manufacturer's instructions. This fragment was cloned into plasmid pShV3 (WO 03/054163) digested with EcoRV, and transformed into *E. coli* XL1 Blue cells according to the manufacturer's instructions (Stratagene, Inc., La Jolla, Calif.). Transformants were selected on 2×YT agar plates supplemented with 100 μg of ampicillin per ml and incubated at 37° C. for 16 hours. Plasmid DNA from several transformants was isolated using QIAGEN tip-20 columns according to the manufacturer's instructions and verified on a 0.8% agarose gel using 0.5×TBE buffer by restriction analysis with SacI/SphI. The resulting plasmid was designated pMRT044.

Plasmid pMRT044 and pNBT3 (pDG268MCSΔNeo-Pr$_{cryIIIA}$/cryIIIAstab/SAV, U.S. Pat. No. 6,255,076) were digested with SacI plus HindIII. The digestions were resolved on a 0.8% agarose gel using 0.5×TBE buffer and the larger vector fragment (approximately bp) from pMRT044 and the smaller cryIIIA stabilizer fragment from pNBT3 were gel-purified using a QIAquick DNA Extraction Kit according to the manufacturer's instructions. The two purified fragments were ligated together with T4 DNA polymerase and the ligation mix was used to transform *E. coli* XL1 Blue cells according to the manufacturer's instructions. Transformants were selected on 2×YT agar plates supplemented with 100 μg of ampicillin per ml and incubated at 37° C. for 16 hours. Plasmid DNA from several transformants was isolated using QIAGEN tip-20 columns according to the manufacturer's instructions and verified on a 0.8% agarose-0.5×TBE gel by restriction analysis with SacI/HindIII. The resulting plasmid was designated pMRT070.

Plasmids pMRT074 (WO 03/054163) and pMRT070 were digested with EcoRI/HindIII. A fragment of approximately 3500 bp from pMRT074 and a fragment of approximately 1100 bp from pMRT070 were isolated from a 0.8% agarose-0.5×TBE gel using a QIAquick DNA purification Kit according to the manufacturer's instructions, ligated, and transformed into *Bacillus subtilis* A168Δ4 competent cells. Transformants were selected on TBAB-agar plates supplemented with 1 μg of erythromycin and 25 μg of lincomycin per ml and incubated at 30° C. for 24-48 hours. Plasmid DNA from several transformants was isolated using QIAGEN tip-20 columns according to the manufacturer's instructions and verified on a 0.8% agarose-0.5×TBE gel by restriction analysis with EcoRI/HindIII. The resulting plasmid was designated pMRT075.

Plasmids pMRT075 and pNBT40 were digested with SacI plus NotI. Plasmid pNBT40 is essentially the pCR2.1—TOPO vector containing a gene (npr[BamP]) encoding a neutral protease from *Bacillus amyliquefaciens* (Vasantha et al., 1984, *J. Bacteriol.* 159(3): 811, accession no. K02497). A DNA fragment of approximately 5500 bp from pMRT075 and a fragment of approximately 1600 bp from pNBT40 were isolated from a 0.8% agarose gel using 0.5×TBE buffer using a QIAquick DNA purification Kit according to the manufacturer's instructions, ligated, and transformed into *Bacillus subtilis* A168Δ4 competent cells. Transformants were selected on TBAB-agar plates supplemented with 1% skim milk, and 1 µg of erythromycin and 25 µg of lincomycin per ml and incubated at 30° C. for 24-48 hours. Transformants producing clearing zones on TBAB-agar skim milk plates were obtained and the resulting plasmid was designated pMRT077.

The JP170 alkaline protease gene (WO 98/56927 and U.S. Pat. No. 5,891,701, accession no. AR069954) was PCR-amplified from *Bacillus* sp. JP170 genomic DNA obtained as described in WO 98/56927 using the primers below. Genomic DNA was prepared according to the procedure described by Pitcher et al., 1989, supra.

```
Primer 992843:
                                       (SEQ ID NO: 39)
5'-CGAGCTCGATGTGTTATAAATTGAGAGGAG-3'

Primer 961252:
                                       (SEQ ID NO: 40)
5'-GCGGCCGCGTCATAAACGTTGCAATCGTGCTC-3'
```

PCR amplifications were conducted in triplicate in 50 µl reactions composed of 50 ng of chromosomal DNA, 0.4 µM each of primers 992843 and 961252, 200 µM each of dATP, dCTP, dGTP, and dTTP, 1×PCR Buffer II with 2.5 mM MgCl$_2$, and 2.5 units of AmpliTaq Gold™ DNA polymerase. The reactions were performed in a RoboCycler 40 thermacycler programmed for 1 cycle at 95° C. for 9 minutes; 30 cycles each at 95° C. for 1 minute, 55° C. for 1 minute, and 72° C. for 1 minute; and 1 cycle at 72° C. for 5 minutes. The PCR product was visualized using a 0.8% agarose gel with 0.5×TBE buffer. The expected fragment was approximately 2163 bp.

The 2163 bp PCR fragment was cloned into pCR2.1 using a TA-TOPO Cloning Kit and transformed into *E. coli* OneShot™ competent cells according to the manufacturer's instructions. Transformants were selected at 37° C. after 16 hours of growth on 2×YT agar plates supplemented with 100 µg of ampicillin per ml. Plasmid DNA was purified from several transformants using a QIAGEN Bio Robot 9600 according to the manufacturer's instructions and analyzed by SacI plus NotI digestion on a 0.8% agarose gel using 0.5×TBE buffer. Plasmids with the correct size inserts were identified and the DNA sequence of the inserts was confirmed by DNA sequencing using M13 (−20) forward and M13 reverse primers and the following internal primers. A plasmid with the correct sequence was identified and designated pNBT39.

```
Primer 992843:
                                       (SEQ ID NO: 39)
5'-CGAGCTCGATGTGTTATAAATTGAGAGGAG-3'

Primer 961021:
                                       (SEQ ID NO: 41)
5'-GTCGAATATGATGGGGATG-3'

Primer 960898:
                                       (SEQ ID NO: 42)
5'-GGACAAGGACAGATTGTAGCAGTTGCTGATACTGG-3'

Primer 961048:
                                       (SEQ ID NO: 43)
5'-GCGATTACAGTTGGGGCAACC-3'

Primer 961222:
                                       (SEQ ID NO: 44)
5'-GGTAGCACGACGGCATCACTAAC-3'
```

Plasmid pNBT39 and pMRT077 were digested with SacI plus NotI. The digestions were resolved on a 0.8% agarose gel using 0.5×TBE buffer and the larger vector fragment from pMRT077 and the smaller JP170 fragment (approximately 2163 bp) from pNBT39 were gel-purified using a QIAquick DNA Extraction Kit according to the manufacturer's instructions. The two purified fragments were ligated together with T4 DNA ligase and the ligation mix was transformed into *Bacillus subtilis* 168Δ4 competent cells. Plasmid DNA was purified from several transformants using QIAGEN tip-20 columns according to the manufacturer's instructions and analyzed by SacI plus NotI digestion on a 0.8% agarose gel using 0.5×TBE buffer. The correct plasmid was identified by the presence of an approximately 2163 bp SacI/NotI JP170 fragment and was designated pTH012.

*Bacillus licheniformis* TH3 was constructed by replacement of the amyL gene of *Bacillus licheniformis* MDT220 with the JP170 protease gene. pTH012 was introduced into *Bacillus licheniformis* MDT220 via electroporation, and then integrated and excised from the chromosome as described previously, replacing the amyL gene with the JP170 alkaline protease gene to create *Bacillus licheniformis* TH3. The desired erythromycin-sensitive clone was identified by protease expression based on the production of halos on TBAB plus 1% dry milk plates.

Construction of *Bacillus licheniformis* Strain MDT223 Containing One-Copy of the P17 Promoter/JP170 Expression Cassette in the amyL Locus and a Second P17 Promoter at the xylA Locus Plasmid pNBT35 (pDG268MCSΔ-Pr$_{short\ "consensus"}$ amyQ/Pr$_{cryIIIA}$/cryIIIAstab/SAV, equivalent to pNBT23 but lacking the neo gene) was digested with SfiI and treated with T4 DNA polymerase to generate blunt ends; the polymerase was heat-inactivated and the plasmid digested with DraIII to remove a fragment upstream of the promoter, bearing the cat gene. Plasmid pNBT32 was digested with Ecl136II and DraIII to release a fragment bearing the amyL4199 promoter and cat gene. The digestions were resolved on a 0.8% agarose gel using 0.5×TBE buffer and the larger vector fragment (approximately 5811 bp) from pNBT35 and the smaller amyL4199 promoter-bearing fragment (approximately 2150 bp) from pNBT32 were gel-purified using a QIAquick DNA Extraction Kit according to the manufacturer's instructions. The two purified fragments were ligated together with T4 DNA ligase, and the ligation mix was transformed into *E. coli* SURE® competent cells according to the manufacturer's instructions. Transformants were selected at 37° C. on 2XYT agar plates supplemented with 100 mg of ampicillin per ml. Plasmid DNA from these transformants was purified using a QIAGEN Bio Robot 9600 (QIAGEN, Valencia, Calif.) according to the manufacturer's instructions and analyzed by digestion with NcoI and electrophoresis on a 0.8% agarose gel using 0.5×TBE buffer. The plasmid was found to have the correct expected fragments (approximately 5492 bp and 2466 bp) and was designated pNBT36. *Bacillus licheniformis* TH4 was constructed by insertion of the cryIIIA promoter at the xylA locus (accession no. Z80222) of *Bacillus licheniformis* TH3. The cryIIIA promoter was PCR-amplified from pNBT36 plasmid DNA using the following primers.

```
Primer 951036:
                                       (SEQ ID NO: 45)
5'-GAGCTCCATAATACATAATTTTCAAACTG-3'

Primer 993396:
                                       (SEQ ID NO: 46)
5'-GTCGACAACGTAAGATGAAACCTTAG-3'
```

PCR amplifications were conducted in triplicate in 50 µl reactions composed of 50 ng of plasmid DNA, 0.4 µM each of primers 951036 and 993396, 200 µM each of dATP, dCTP, dGTP, and dTTP, 1×PCR Buffer II with 2.5 mM $MgCl_2$, and 2.5 units of AmpliTaq Gold™ DNA polymerase. The reactions were performed in a RoboCycler 40 thermacycler programmed for 1 cycle at 95° C. for 9 minutes; 30 cycles each at 95° C. for 1 minute, 55° C. for 1 minute, and 72° C. for 1 minute; and 1 cycle at 72° C. for 5 minutes. The PCR product was visualized using a 0.8% agarose gel using 0.5×TBE. The expected fragment was approximately 622 bp.

The 622 bp PCR fragment was cloned into pCR2.1 using the TA-TOPO Cloning Kit and transformed into *E. coli* OneShot™ competent cells according to the manufacturer's instructions. Transformants were selected at 37° C. after 16 hours of growth on 2×YT agar plates supplemented with 100 µg of ampicillin per ml. Plasmid DNA from these transformants was purified using a QIAGEN Bio Robot 9600 according to the manufacturer's instructions and digested with SacI plus NotI. Plasmids were identified and the DNA sequence of the inserts was confirmed by DNA sequencing using M13 (−20) forward and M13 reverse primers. A plasmid with the correct sequence was designated pNBT41.

Plasmid pNBT41 was digested with SalI and Ecl136 µl to excise the promoter and cryIIIA stabilizer fragment. Plasmid pSJ5218 (containing a 5' fragment of *Bacillus licheniformis* xylR and an internal fragment of xylA; U.S. Patent Application No. 20030032186) was digested with SalI and Bst1071. The digestions were resolved on a 0.8% agarose gel using 0.5×TBE buffer and the larger vector fragment (approximately 6381 bp) from pSJ5218 and the smaller cryIIIA stabilizer fragment (approximately 622 bp) from pNBT41 were gel-purified using a QIAquick DNA Extraction Kit according to the manufacturer's instructions.

The two purified fragments were ligated together with T4 DNA ligase and the ligation mix was transformed into *Bacillus subtilis* 168Δ4. Plasmid DNA was purified from several transformants using QIAGEN tip-20 columns according to the manufacturer's instructions and analyzed by restriction enzyme or PCR analysis. The correct plasmid was identified and was designated pTH009. Plasmid pTH009 was introduced into *Bacillus licheniformis* TH3 via electroporation and integrated by selection for erythromycin resistance at 50° C. Desired integrants were identified by the inability to grow on minimal medium supplemented with 0.5% xylose (U.S. Patent Application No. 20030032186) due to insertion into the xylA gene. The plasmid was excised as described previously to create *Bacillus licheniformis* TH4, which contained the cryIIIA promoter at the xylA locus. The desired erythromycin-sensitive strain was identified by the inability to grow on minimal medium supplemented with 0.5% xylose as the carbon source and by PCR analysis.

*Bacillus licheniformis* MDT223 was constructed by insertion of the remainder of the P17 triple tandem promoter at the xylA locus of *Bacillus licheniformis* TH4. The P17 triple tandem promoter, minus the mRNA-stabilizing Shine-Dalgarno sequence, was PCR-amplified from pNBT36 plasmid DNA using primers 993397 and 993398 shown below and cloned into pCR2.1 using the TOPO-TA Cloning Kit.

```
Primer 993397:
                                    (SEQ ID NO: 47)
5'-GTCGACCGCTCGCTTTCCAATCTGA-3'
```

```
Primer 993398:
                                    (SEQ ID NO: 48)
5'-GAATTCAATAATTTATACACTATTCTATTGG-3'
```

PCR amplifications were conducted in triplicate in 50 µl reactions composed of 50 ng of plasmid DNA, 0.4 µM each of primers 993397 and 993398, 200 µM each of dATP, dCTP, dGTP, and dTTP, 1×PCR Buffer II with 2.5 mM $MgCl_2$, and 2.5 units of AmpliTaq Gold™ DNA polymerase. The reactions were performed in a RoboCycler 40 thermacycler programmed for 1 cycle at 95° C. for 9 minutes; 30 cycles each at 95° C. for 1 minute, 55° C. for 1 minute, and 72° C. for 1 minute; and 1 cycle at 72° C. for 5 minutes. The PCR product was visualized using a 0.8% agarose gel with 0.5×TBE buffer. The expected fragment was approximately 992 bp.

The 992 bp PCR fragment was cloned into pCR2.1 using the TA-TOPO Cloning Kit and transformed into *E. coli* OneShot™ competent cells according to the manufacturer's instructions. Transformants were selected at 37° C. after 16 hours of growth on 2×YT agar plates supplemented with 100 µg of ampicillin per ml. Plasmid DNA from these transformants was purified using a QIAGEN Bio Robot 9600 according to the manufacturer's instructions. The DNA sequence of the inserts was confirmed by DNA sequencing using M13 (−20) forward and M13 reverse primers. A plasmid with the correct sequence was identified and designated pTH027.

Plasmid pTH027 was digested with EcoRI plus SalI. Plasmid pSJ5218 was digested with EcoRI and SalI to remove the xylA fragment and spectinomycin-resistance gene. The digestions were resolved on a 0.8% agarose gel using 0.5×TBE buffer and the larger vector fragment from pSJ5218 and the smaller fragment (approximately 992 bp) from pNBT41 were gel-purified using a QIAquick DNA Extraction Kit according to the manufacturer's instructions. The two purified fragments were ligated together with T4 DNA ligase and the ligation mix was transformed into *Bacillus subtilis* 168Δ4. Plasmid DNA was purified from several transformants using QIAGEN tip-20 columns according to the manufacturer's instructions and analyzed restriction enzyme digestion and/or PCR analysis. The correct plasmid was identified and was designated pTH010.

Plasmid pTH010 was introduced into *Bacillus licheniformis* TH4 via electroporation and integrated by selection for erythromycin resistance at 50° C. as described previously. PCR analysis was used to identify integrants with pTH010 inserted at the xylA locus. The plasmid was excised as described previously, and erythromycin-sensitive excision products were screened for presence of the triple promoter at xylA by PCR analysis. One such strain was designated *Bacillus licheniformis* MDT223.

Construction of *Bacillus licheniformis* Strain TH6 Containing One-Copy of the P17 Promoter/Mannanase Expression Cassette in the amyL Locus and a Second P17 Promoter at the xylA Locus TH6 was constructed by replacement of the JP170 protease gene of MDT223 with a mannanase gene. Plasmid pMB1242 contains the amyL ribosome-binding site (RBS) followed by the coding sequence for a fusion of the AmyL signal peptide to the mature mannanase of alkalophilic *Bacillus* sp. 1633 (Sequence ID NO:1 in WO 99/64619), truncated at the C-terminus. The RBS and mannanase gene were PCR-amplified from pMB1242 using primers 993634 and 990498.

Primer 993634:
(SEQ ID NO: 49)
5'-GTTAACTTGAAAAACGGTGCTTAATC-3'

Primer 990498:
(SEQ ID NO: 50)
5'-TGGTACTGGCCTTAAGGGCCGAATATTTATACAATATCATGAGCTC
CACATTGAAAGGG-3'

The gene was cloned into pCR2.1 using the TOPO-TA Cloning Kit, creating pNBT45. pNBT45 and pNBT18 (pDG268MCSΔNeo-cry3A stabilizer/SAV, U.S. Pat. No. 6,255,076) were digested with SacI and HpaI. The digestions were resolved on a 0.8% agarose gel using 0.5×TBE buffer and the larger vector fragment from pNBT18 (approximately 7330 bp) and the smaller mannanase-bearing fragment (approximately 1008 bp) from pNBT45 were gel-purified using a QIAquick DNA Extraction Kit according to the manufacturer's instructions. The two purified fragments were ligated together with T4 DNA ligase and the ligation mix was transformed into Bacillus subtilis 168Δ4. Plasmid DNA was purified from several transformants using QIAGEN tip-20 columns according to the manufacturer's instructions and analyzed restriction enzyme digestion and/or PCR analysis. The correct plasmid was identified and was designated pNBT46.

pNBT46 and pTH012 were digested with SacI and NotI. The digestions were resolved on a 0.8% agarose gel using 0.5×TBE buffer and the larger vector fragment from pTH012 (approximately 5359 bp) and the smaller fragment from pNBT46 (approximately 1098 bp), bearing the mannanase gene and aprH terminator, were gel-purified using a QIAquick DNA Extraction Kit according to the manufacturer's instructions. The two purified fragments were ligated together with T4 DNA ligase and the ligation mix was transformed into Bacillus subtilis 168Δ4. Plasmid DNA was purified from several transformants using QIAGEN tip-20 columns according to the manufacturer's instructions and analyzed restriction enzyme digestion and/or PCR analysis. The correct plasmid was identified and was designated pTH013.

Plasmid pTH013 was introduced into Bacillus licheniformis MDT223 via electroporation and integrated by selection for erythromycin resistance at 50° C. as described previously. Integrants with pTH013 integrated at the amyL locus were identified by a reduction in the size of zones of clearing on TBAB-agar plates supplemented with 1% skim milk, indicating disruption of the JP170 protease expression cassette. The plasmid was excised as described previously, and erythromycin-sensitive excision products were screened for inability to form clearing zones on TBAB-agar skim milk plates. The presence of the triple promoter/mannanase expression cassette at amyL was verified by PCR analysis. One such strain was designated Bacillus licheniformis TH6.

Example 7. Construction of a Strain of Bacillus licheniformis, Having in its Chromosome an Expression Cassette Containing Two Open Reading Frames in a Closely Spaced, Parallel Configuration, Both Encoding Protease 10R (where One Open Reading Frame Encodes a Protein with a Two Amino Acid Extension)

B. subtilis strains, that are able to transfer the integration vector plasmid designed for integration of the tandem gene construct at the amyL locus into B. licheniformis, were constructed by transformation of plasmids pSJ7365 and pSJ7366 into competent cells of B. subtilis PP289-5. PP289-5 (U.S. Pat. No. 6,066,473) contains a deletion in the dal gene (and is therefore able to grow only if media are supplemented with D-alanine), and contains plasmids pLS20 and pBC16, which together deliver the functions needed for conjugative transfer of the integration vector plasmid.

Transformants were selected on LB PG Sk plates (LB plates with phosphate (0.01 M $K_3PO_4$), glucose (0.4%), and skimmed milk (1%)), supplemented with erythromycin (5 μg/ml), tetracycline (5 μg/ml), and D-alanine (100 μg/ml), at 30° C. The following strains were kept: SJ7369 and SJ7370 (both PP289-5/pSJ7365), and SJ7371 and SJ7372 (both PP289-5/pSJ7366).

Strain TH6, described above, can be used as recipient in conjugations with each of donor strains SJ7369 to SJ7372, performed as described in U.S. Pat. No. 6,066,473. Briefly, donor and recipient cells from overnight plates are mixed on LBPSG agar plates (LB plates with phosphate (0.01 M $K_3PO_4$), glucose (0.4%), and starch (0.5%)), supplemented with D-alanine (100 μg/ml), incubated at 30° C. for 5 hours, and the plates subsequently replica plated onto LB PG Sk plates with erythromycin (2 μg/ml). Colonies are subsequently streaked on LB PG Sk plates with erythromycin (5 μg/ml), +/−tetracycline (5 μg/ml), and tetracycline-sensitive (indicating absence of pBC16), protease-positive transconjugants are streaked onto LB PG Sk plates with erythromycin (5 μg/ml), which are incubated at 50° C. over the weekend. The selection for erythromycin resistance at high temperature ensures that colonies formed have arisen by integration of the integration vector plasmid into the B. licheniformis host strain chromosome, by homologous recombination at either the cryIIIA_stab or the dws_amyL sequence, as the plasmid is unable to replicate as a free plasmid at this temperature.

Colonies forming at 50° C. are streaked onto LB PG Sk plates and incubated at 30° C. overnight. This temperature allows the replication of the integrated plasmid, which facilitates its excision from the chromosome, and ultimately loss from the cell (indicated by erythromycin sensitivity). The plasmid may excise via the same region of homology, as was used for integration, in which case the resulting cell is identical to the host strain. The plasmid may alternatively excise via the other region of homology (e.g. integration via cryIIIA_stab, and excision via dws_amyL, or vice versa) in which case the tandem expression cassette is left in the chromosome. Cells from protease-positive regions of the plates are streaked onto new LB PG Sk plates and incubated at 30° C. overnight. Cells from protease-positive regions of these plates are streaked onto new LB PG Sk plates and incubated at 30° C. overnight, whereafter plates are replica plated to plates with and without erythromycin. Protease positive, erythromycin sensitive strains are kept.

Such strains will in their chromosome, at the amyL locus, contain an expression cassette consisting of a strong composite promoter region (PamyL_4199/scBAN/cryIIIA+stab) driving expression of a bicistronic construct, carrying SEQUENCE ID NO: 1, encoding protease 10R, followed by SEQUENCE ID NO: 2, encoding protease 10R with a two amino acid extension.

The strains can be evaluated by shake flask fermentation, by inoculation into PS-1 medium and incubation at 30° C. for 7 days, at 300 rpm, and the protease activity of full culture samples can be determined, using the PNA assay with succinyl-alanine-alanine-proline-phenylalnine-paranitroanilide as a substrate. The principle of the PNA assay is described in Rothgeb, T. M., Goodlander, B. D., Garrison, P.

H., and Smith, L. A., Journal of the American Oil Chemists' Society, Vol. 65 (5) pp. 806-810 (1988).

It is possible to make the integration of the bicistronic construct at several, different chromosomal locations, as described in WO 02/00907.

It is possible to make a double, triple, quadruple or even higher tandem construct by using a larger number of different DNA sequences encoding the same enzyme. As an example a construct can be made, which contains the sequence given in SEQ ID NO's: 1 and 2.

The genetic stability of the resulting strains can be investigated, e.g. by extraction of DNA following prolonged fermentation, and detection of the integrated construct composed of two, three, four or even more different sequences encoding the same polypeptide by Southern blot procedures. By proper choice of restriction enzymes and probes, Southern blotting can reveal whether copy loss has occurred by recombination between integrated sequences.

Example 8. Construction of a *Bacillus licheniformis* Strain, SJ7013, Having Two Copies of the SEQUENCE ID NO: 1, Encoding Protease 10R, Integrated at Two Different Locations in the Chromosome Plasmid pSJ6869, designed to allow integration of the SEQUENCE ID NO: 1 expression cassette into the chromosome of a *B. licheniformis* strain, that already contains a triple promoter integrated at the amyL locus, was described in example 3.

Plasmid pSJ6869 was introduced into *B. licheniformis* TH6 (described in example 6) by conjugation from a *B. subtilis* donor strain, SJ6885 (PP289-5/pSJ6869), prepared as described in example 7. The protease gene, encoded by SEQUENCE ID NO: 1, was subsequently inserted into the chromosome at the amyL locus by the procedure described in example 7. A resulting strain was kept as SJ6924.

Plasmid pSJ6408 is an integration vector designed to allow integration of cryIIIA stabilizer containing expression cassettes at the xylA locus of *B. licheniformis* host strains, that already contains an integrated copy of the triple promoter (the amyL4199/scBAN/cry3A triple tandem promoter) at this locus. It was constructed by ligation of the 0.4 kb EcoRI-HindIII fragment from pSJ5131 (described in International Patent Application WO 02/00907, page 43) to the 4.3 kb EcoRI-HindIII fragment of pSJ2739 (U.S. Pat. No. 5,882,888, column 27). The ligation mixture was transformed into competent cells of *B. subtilis* DN1885, selecting erythromycin-resistance at 30° C. Two transformants were kept, SJ6408 (DN1885/pSJ6408) and SJ6409 (DN1885/pSJ6409).

Plasmid pSJ6422 was constructed by insertion of the 1.8 kb BglII fragment containing the protease 10R gene from pSJ6074 (described in example 1) into BglII-digested pSJ6408. The ligation mixture was transformed into competent cells of *B. subtilis* PL1801, selecting erythromycin-resistance at 30 □ C, and two transformants kept as SJ6422 (PL1801/pSJ6422) and SJ6423 (PL1801/pSJ6423).

Plasmid pSJ6973 is similar to pSJ6422, except that it contains the protease 10R gene having the SEQUENCE ID NO: 1 sequence. It was constructed by excision of the 1.2 kb BslI-MluI fragment containing the SEQUENCE ID NO: 1 gene from pSJ6869, and ligation of this fragment with the 2.2 kb MluI-BslI fragment from pSJ6422 and the 3.2 kb BslI-BslI fragment from pSJ6422. The ligation mixture was transformed into competent cells of *B. subtilis* PL1801, selecting erythromycin-resistance at 30 □ C, and two transformants kept as SJ6973 (PL1801/pSJ6973) and SJ6974 (PL1801/pSJ6974).

Plasmid pSJ6973 was introduced into *B. licheniformis* SJ6924 (the one-copy strain described above) by conjugation from a *B. subtilis* donor strain, SJ6983 (PP289-5/pSJ6973), prepared as described in example 7. Tetracyclin-sensitive transconjugants were spread on TSS minimal media plates supplemented with xylose, as described in Patent Publication WO 02/00907, and incubated at 5□ C. Strains, in which the desired integrati on event had restored the chromosomal xylAB operon, were picked as brownish coloured colonies on the TSS-xylose plates, and propagated in liquid TY cultures ⊡ C, 30 to allow plasmid replication, excision, and loss from the cells. Culture samples were plated on TSS-xylose plates, and brownish coloured, erythromycin-sensitive colonies were isolated. One such strain, having one copy of the 10R SEQUENCE ID NO: 1 gene at the amyL locus, and another copy of the 10R SEQUENCE ID NO: 1 gene at the xyl locus, was kept as SJ7013.

Example 9. Construction of *B. licheniformis* Strains SJ7386 and SJ7387, Having One Copy of the SEQUENCE ID NO: 51, Encoding Protease 10R, Integrated at the amyL Locus pSJ7305 is a pUC19 based plasmid with the same structure as pSJ6074, with the difference that the Savinase® signal peptide-10Rpro+mature coding region consists of another synthetic DNA fragment with a DNA sequence different from that of pSJ6074, but still encoding the same amino acid sequence as the gene on pSJ6074. The synthetic coding region has the sequence given as SEQ ID NO: 51. DNA containing this synthetic coding region was used as template in a PCR amplification with primers

388968:

(SEQ ID NO: 52)

5'-gactgaattcgagctctataaaaatgaggagggaaccgaatgaaaaaacctttgggaaaaatcg, and

388969:

(SEQ ID NO: 53)

5'-gactaagcttacgcgttatgttctaagtcttactcccc

The annealing temperature was ramped down from 59° C. to 49° C., then kept constant at 54° C. A correctly sized PCR fragment was obtained, digested with SacI+MluI, and ligated to the 3.3 kb MluI-SacI fragment of pSJ6074. The ligation mixture was transformed into *E. coli* SJ2 by electroporation. The PCR amplified region was DNA sequenced on plasmids, that by restriction digests were found to contain the desired insert. A plasmid having the correct DNA sequence was kept in strain SJ7305 (SJ2/pSJ7305).

Plasmid pSJ7312 is designed to allow integration of the SEQ ID NO: 51 expression cassette into the chromosome of a *B. licheniformis* strain, that already contains a triple-promoter (the amyL4199/scBAN/cryIIIA triple tandem promoter) integrated at the amyL locus, by homologous recombination at the cryIIIA stabilizer and downstream amyL segments.

It was constructed by excision of the 1.8 kb EcoRI-HindIII fragment from pSJ7305, and ligation of this fragment to the 4.6 kb EcoRI-HindIII fragment of plasmid pSJ5487 (described in example 3). The ligation mixture was transformed into B. subtilis PL1801 competent cells, selecting erythromycin resistance (2 microgram/ml) at 30° C. 6 protease-positive transformants, forming halos on plates supplemented with skimmed milk, were analysed by restriction digest, and found to be correct. 2 were kept, SJ7311 (PL1801/pSJ7311) and SJ7312 (PL1801/pSJ7312).

Plasmid pSJ7312 was introduced into B. licheniformis TH6 (described in example 6) by conjugation from a B. subtilis donor strain, SJ7321 (PP289-5/pSJ7312), prepared as described in example 7. The protease gene, encoded by SEQUENCE ID NO: 51, was subsequently inserted into the chromosome at the amyL locus by the procedure described in example 7. A resulting strain was kept as SJ7387.

Example 10. Construction of a B. licheniformis Strains SJ7430 and SJ7431, Having One Copy of the Tandem Gene Construct SEQUENCE ID NO: 1-SEQUENCE ID NO: 51, Integrated at the amyL Locus Plasmid pSJ7420 is an integration vector plasmid for integration of the tandem gene construct SEQUENCE ID NO: 1—SEQUENCE ID NO: 51 at the amyL locus in B. licheniformis. It was constructed in the following steps:

Plasmid pSJ7351 was constructed by PCR amplification using pSJ6996 (described in example 4) as template, and primers

```
#393822:
                                     (SEQ ID NO: 54)
5'-gactgaattcacgcgtgagctctataaaaatgaggaggg and

393823:
                                     (SEQ ID NO: 55)
5'-gactaagcttgctagcctaatgtgttgtacggagtc
```

The annealing temperature was ramped down from 58° C. to 48° C., then kept constant at 53° C. A correctly sized PCR fragment was obtained, digested with EcoRI+HindIII, and the 1.2 kb fragment ligated to EcoRI+HindIII digested pUC19 vector. The ligation mixture was transformed into E. coli SJ2 by electroporation, and a transformant was kept as SJ7351 (SJ2/pSJ7351).

Plasmid pSJ7402 was constructed by excision of the 10R SEQ ID NO: 51 gene from pSJ7305 on a 1.2 kb SacI-HindIII fragment, and ligation of this fragment to the 2.7 kb HindIII-SacI fragment of pSJ7351. The ligation mixture was transformed into E. coli SJ2 by electroporation, and two transformants were kept as SJ7402 (SJ2/pSJ7402) and SJ7403 (SJ2/pSJ7403).

Plasmid pSJ7404, carrying the tandem gene construct SEQUENCE ID NO: 1-SEQUENCE ID NO: 51, was constructed by excision of the 1.1 kb MluI fragment from pSJ7402, and insertion of this fragment into MluI-digested pSJ6814 (described in example 3). The ligation mixture was transformed into E. coli SJ2 by electroporation, and two transformants were kept as SJ7404 (SJ2/pSJ7404) and SJ7405 (SJ2/pSJ7405).

Plasmid pSJ7420 was finally constructed by excision of the tandem gene construct on a 2.9 kb EcoRI-HindIII fragment from pSJ7404, and ligation of this fragment to the 4.8 kb EcoRI-HindIII fragment of pSJ5487 (described in example 3). The ligation mixture was transformed into B. subtilis PL1801 competent cells, selecting erythromycin resistance (2 microgram/ml) at 30° C. 6 protease-positive transformants, forming halos on plates supplemented with skimmed milk, were analysed by restriction digest, and found to be correct. 2 were kept, SJ7420 (PL1801/pSJ7420) and SJ7421 (PL1801/pSJ7421).

It was again observed, that plasmid DNA prepared from these strains revealed no sign of recombination between the tandemly arranged, parallel open reading frames encoding identical enzymes, but differing in their DNA sequence. It is of particular interest, given that the vector plasmid is based on pE194, which is a rolling circle replicating plasmid of the kind on which tandem repeats are notoriously unstable (Gruss and Ehrlich, 1989, Microbiological reviews, 53(2), 231-241).

Plasmids pSJ7420 and pSJ7421 were introduced into B. licheniformis TH6 (described in example 6) by conjugation from B. subtilis donor strains, SJ7422 (PP289-5/pSJ7422) and SJ7424 (PP289-5/pSJ7424), prepared as described in example 7. The tandem protease gene construct, consisting of SEQUENCE ID NO: 1 followed by SEQUENCE ID NO: 51, was subsequently inserted into the chromosome at the amyL locus by the procedure described in example 7. Resulting strains were kept as SJ7430 (from pSJ7420) and SJ7431 (from pSJ7421).

Example 11. Construction of B. licheniformis Strains SJ7502 to SJ7507, Having Two Copies of the Tandem Gene Construct SEQUENCE ID NO: 1—SEQUENCE ID NO: 51, Integrated at Two Different Locations in the Chromosome Plasmid pSJ7465 for integration of the cryIIIA stabilizer SEQUENCE ID NO: 1—SEQUENCE ID NO: 51 construct into the xyl locus of B. licheniformis host strains, that already contains an integrated copy of the triple promoter (the amyL4199/scBAN/cry3A triple tandem promoter) at this locus, was constructed by excision of the 1.8 kb StuI-NotI fragment from pSJ7420 (described in example 10) and ligation of this fragment to the 6.0 kb StuI-NotI fragment of pSJ6974 (described in example 8). The ligation mixture was transformed into competent cells of B. subtilis PL1801, selecting erythromycin-resistance at 30° C., and two transformants kept as SJ7465 (PL1801/pSJ7465) and SJ7466 (PL1801/pSJ7466).

Plasmids pSJ7465 and pSJ7466 were introduced into B. licheniformis SJ6930 (the one-copy tandem-construct strain described in example 10) by conjugation from B. subtilis donor strains SJ7467 and SJ7468 (both PP289-5/pSJ7465) or from SJ7470 (PP289-5/pSJ7466), prepared as described in example 7. Tetracyclin-sensitive transconjugants were spread on TSS minimal media plates supplemented with xylose, as described in Patent Publication WO 02/00907, and incubated at 50 □ C. Strains, in which the desired integration event had restored the chromosomal xylAB operon, were picked as brownish coloured colonies on the TSS-xylose plates, and propagated in liquid TY cultures at 30° C., to allow plasmid replication, excision, and loss from the cells. Culture samples were plated on TSS-xylose plates, and brownish coloured, erythromycin-sensitive colonies were isolated. Such strains, having one copy of the 10R SEQUENCE ID NO: 1—SEQUENCE ID NO: 51 tandem gene construct at the amyL locus, and another copy of the 10R SEQUENCE ID NO: 1—SEQUENCE ID NO: 51 tandem gene construct at the xyl locus, were kept as SJ7502 and SJ7503 (obtained using pSJ7465 via strain SJ7467), SJ7504 and SJ7505 (obtained using pSJ7465 via strain SJ7468), and SJ7506 and SJ7507 (obtained using pSJ7466 via strain SJ7470).

Example 12. Evaluation of Strains by Shake Flask Fermentation

Strains constructed as described in the preceding examples were evaluated by shake flask fermentations and protease assays as described in example 7. In one series of fermentations the following relative yields were obtained, taking the yield from strain SJ7013 having two copies of SEQUENCE ID NO: 1 at two different locations in the chromosome as 100% (average of duplicate shake flasks):

| | | |
|---|---|---|
| SJ7013: | 100% | |
| SJ7387: | 86% | (1 copy, SEQUENCE ID NO: 51) |
| SJ7430: | 107% | (1 copy, SEQUENCE ID NO: 1- |

| | | |
|---|---|---|
| SJ7431: | 103% | SEQUENCE ID NO: 51) (as SJ7430) |

In another series the following relative yields were obtained, taking again the yield from strain SJ7013 as 100% (average of duplicate shake flasks):

| | | |
|---|---|---|
| SJ7013: | 100% | |
| SJ7502: | 123% | (2 copies, SEQUENCE ID NO: 1-SEQUENCE ID NO: 51) |
| SJ7503: | 118% | (as SJ7502) |
| SJ7504: | 125% | (as SJ7502) |
| SJ7505: | 125% | (as SJ7502) |
| SJ7506: | 125% | (as SJ7502) |
| SJ7507: | 125% | (as SJ7502) |

The yields from the tandem constructs compare favourably with the yield from the strain having two separately integrated gene copies, indicating stability and efficiency of the tandem gene constructs.

The invention claimed is:

1. A *Bacillus* host cell comprising at least two recombinant open reading frames stably integrated in the same orientation into the host cell chromosome,
   wherein the at least two open reading frames encode enzymes having an identical full-length amino acid sequence;
   wherein the at least two open reading frames differ by at least one nucleotide;
   wherein the at least two open reading frames have no segments greater than 50 bp in length with 100% sequence identity; and
   wherein the enzymes having an identical amino acid sequence are selected from the group consisting of hydrolases, isomerases, ligases, lyases, oxidoreductases, and transferases.

2. The *Bacillus* host cell of claim 1, wherein the at least two open reading frames have no segments greater than 40 bp in length with 100% sequence identity.

3. The *Bacillus* host cell of claim 1, wherein the at least two open reading frames have no segments greater than 30 bp in length with 100% sequence identity.

4. The *Bacillus* host cell of claim 1, wherein the at least two open reading frames have no segments greater than 20 bp in length with 100% sequence identity.

5. The *Bacillus* host cell of claim 1, wherein the at least two open reading frames have no segments greater than 10 bp in length with 100% sequence identity.

6. The *Bacillus* host cell of claim 1, wherein the at least two open reading frames are integrated in the same location on the host cell chromosome.

7. The *Bacillus* host cell of claim 6, wherein the at least two open reading frames are transcribed as a polycistronic mRNA.

8. The *Bacillus* host cell of claim 1, which is a *Bacillus amyloliquefaciens* strain.

9. The *Bacillus* host cell of claim 1, which is a *Bacillus licheniformis* strain.

10. The *Bacillus* host cell of claim 1, which is a *Bacillus subtilis* strain.

11. The *Bacillus* host cell of claim 1, wherein the enzyme is a protease.

12. The *Bacillus* host cell of claim 11, wherein the protease is a serine protease.

13. The *Bacillus* host cell of claim 12, wherein the serine protease is of protease family S2A or S1E.

14. The *Bacillus* host cell of claim 13, wherein the serine protease is encoded by a sequence of SEQ ID NO: 1, 2, or 51.

15. A method of producing enzymes having the same amino acid sequence, comprising the steps of:
   (a) culturing the *Bacillus* host cell of claim 1 under conditions conducive for the expression of the enzymes; and optionally
   (b) recovering the enzymes.

16. A method of producing enzymes having the same amino acid sequence, comprising the steps of:
   (a) culturing the *Bacillus* host cell of claim 2 under conditions conducive for the expression of the enzymes; and optionally
   (b) recovering the enzymes.

17. A method of producing enzymes having the same amino acid sequence, comprising the steps of:
   (a) culturing the *Bacillus* host cell of claim 3 under conditions conducive for the expression of the enzymes; and optionally
   (b) recovering the enzymes.

18. A method of producing enzymes having the same amino acid sequence, comprising the steps of:
   (a) culturing the *Bacillus* host cell of claim 4 under conditions conducive for the expression of the enzymes; and optionally
   (b) recovering the enzyme.

19. A method of producing enzymes having the same amino acid sequence, comprising the steps of:
   (a) culturing the *Bacillus* host cell of claim 5 under conditions conducive for the expression of the enzymes; and optionally
   (b) recovering the enzymes.

* * * * *